United States Patent
Maeda

(10) Patent No.: US 11,452,799 B2
(45) Date of Patent: Sep. 27, 2022

(54) ELASTOMER MOLDED BODY FOR MEDICAL DEVICE, METHOD OF MANUFACTURING OF ELASTOMER MOLDED BODY FOR MEDICAL DEVICE, AND MEDICAL DEVICE

(71) Applicant: OLYMPUS CORPORATION, Hachioji (JP)

(72) Inventor: Issei Maeda, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 471 days.

(21) Appl. No.: 16/726,736

(22) Filed: Dec. 24, 2019

(65) Prior Publication Data

US 2020/0147274 A1 May 14, 2020

Related U.S. Application Data

(63) Continuation of application No. PCT/JP2018/013115, filed on Mar. 29, 2018.

(30) Foreign Application Priority Data

Jul. 7, 2017 (JP) .............................. JP2017-133872

(51) Int. Cl.
*A61L 29/12* (2006.01)
*A61B 1/00* (2006.01)
*B29B 7/90* (2006.01)
*B29C 45/00* (2006.01)
*B29K 509/02* (2006.01)
*B29L 31/00* (2006.01)

(52) U.S. Cl.
CPC .......... *A61L 29/126* (2013.01); *A61B 1/0011* (2013.01); *B29B 7/90* (2013.01); *B29C 45/0001* (2013.01); *B29K 2509/02* (2013.01); *B29L 2031/753* (2013.01)

(58) Field of Classification Search
CPC .......... A61L 29/126; B29C 2045/0015; B29C 70/62; B29C 70/64
See application file for complete search history.

(56) References Cited

FOREIGN PATENT DOCUMENTS

| | | |
|---|---|---|
| EP | 2471561 A1 | 7/2012 |
| JP | H08142236 A | 6/1996 |
| JP | H1132978 A | 2/1999 |
| JP | 2005245517 A | 9/2005 |
| JP | 2017210994 A | 11/2017 |
| JP | 2018048725 A | 3/2018 |
| WO | 2011126017 A1 | 10/2011 |

OTHER PUBLICATIONS

International Search Report (ISR) (and English language translation thereof) dated Jun. 26, 2018 issued in counterpart International Application No. PCT/JP2018/013115.

*Primary Examiner* — James Sanders
(74) *Attorney, Agent, or Firm* — Holtz, Holtz & Volek PC

(57) ABSTRACT

An elastomer molded body for a medical device includes an elastomer portion and a filler. The elastomer portion contains a crosslinked fluorine-based elastomer. The filler is formed from a plurality of particles each of which has aspect ratio of 5 or more and specific surface area of 3 m²/g or more and 10 m²/g or less. The aspect ratio is defined as a ratio of a dimension in a long axis direction thereof to a dimension in a short axis direction thereof. The filler has an uneven distribution in a surface layer part of the elastomer portion and is oriented in a direction along a surface of the elastomer molded body.

12 Claims, 6 Drawing Sheets

ELASTOMER MOLDED BODY FOR MEDICAL DEVICE, METHOD OF MANUFACTURING OF ELASTOMER MOLDED BODY FOR MEDICAL DEVICE, AND MEDICAL DEVICE

The application is a continuation application based on a PCT Patent Application No. PCT/JP2018/013115, filed Mar. 29, 2018, whose priority is claimed on Japanese Patent Application No. 2017-133872, filed Jul. 7, 2017. The content of both the PCT Application and the Japanese Application are incorporated herein by reference.

FIELD OF THE INVENTION

The present invention relates to an elastomer molded body for a medical device, a method of manufacturing of an elastomer molded body for a medical device, and a medical device.

Description of Related Art

Medical devices are disinfected and sterilized before and after use in many cases. Therefore, it is required for a member constituting a medical device to have sufficient resistance such that the physical properties necessary for operation of the medical device are maintained even after repeated disinfection and sterilization treatments. For example, it is required for a member constituting a medical device to have sufficient chemical resistance and heat resistance such that deterioration in physical properties such as strength, lubricity, and flexibility is reduced even after repeated disinfection and sterilization treatments.

For example, PCT International Publication No. WO2016017 and Japanese Unexamined Patent Application, First Publication No. H11-32978 propose an elastomer formed article for an endoscope and an outer cover for a bending portion of an endoscope which have improved physical resistance according to addition of a formulatory agent such as carbon and alumina to a main agent which is a fluorine-based elastomer having excellent chemical resistance.

For example, Japanese Unexamined Patent Application, First Publication No. 2005-245517 proposes an elastomer molded body for an endoscope that has improved resistance with respect to a disinfection treatment and a sterilization treatment according to inclusion of two or more types of a crosslinkable fluorine-based elastomer main agent.

SUMMARY OF THE INVENTION

An elastomer molded body for a medical device according to a first aspect of the present invention includes an elastomer portion containing a crosslinked fluorine-based elastomer, and a filler is formed from a plurality of particles having an aspect ratio of 5 or more, which is defined as a ratio of a dimension in the long axis direction thereof to a dimension in the short axis direction thereof, and specific surface area of $3\ m^2/g$ or more and $10\ m^2/g$ or less, and the filler has an uneven distribution in a surface layer part of the elastomer portion and is oriented in a direction along a surface of the elastomer molded body.

A medical device according to a second aspect of the present invention includes the elastomer molded body for a medical device according to the first aspect.

A method of manufacturing of an elastomer molded body for a medical device according to a third aspect of the present invention includes kneading a molding material containing an uncrosslinked fluorine-based elastomer and filler particles that have an aspect ratio of 5 or more, which is defined as a ratio of a dimension in the long axis direction thereof to a dimension in the short axis direction thereof, and specific surface area of $3\ m^2/g$ or more and $10\ m^2/g$ or less to form a kneaded material having a Mooney viscosity $ML_{1-10}$ (100° C.) of 30 M or more and 40 M or less; and injecting the kneaded material into a molding space of a mold at a flow rate of 30 mm/min or more and 150 mm/min or less to mold the kneaded material.

DETAILED DESCRIPTION OF THE INVENTION

Figure 1:
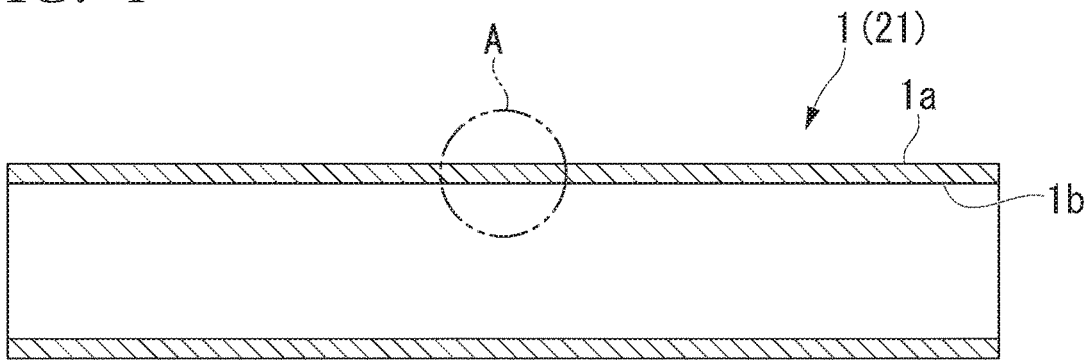
FIG. 1 is a cross-sectional view schematically showing an example of an elastomer molded body for a medical device according to a first embodiment of the present invention.

In the follow embodiments of the present invention will be described with reference to the drawings. In all the drawings, the same or corresponding members are denoted with the same reference numerals in different embodiments, and common descriptions are omitted.

First Embodiment

An elastomer molded body for a medical device according to a first embodiment of the present invention will be described.

Figure 2:
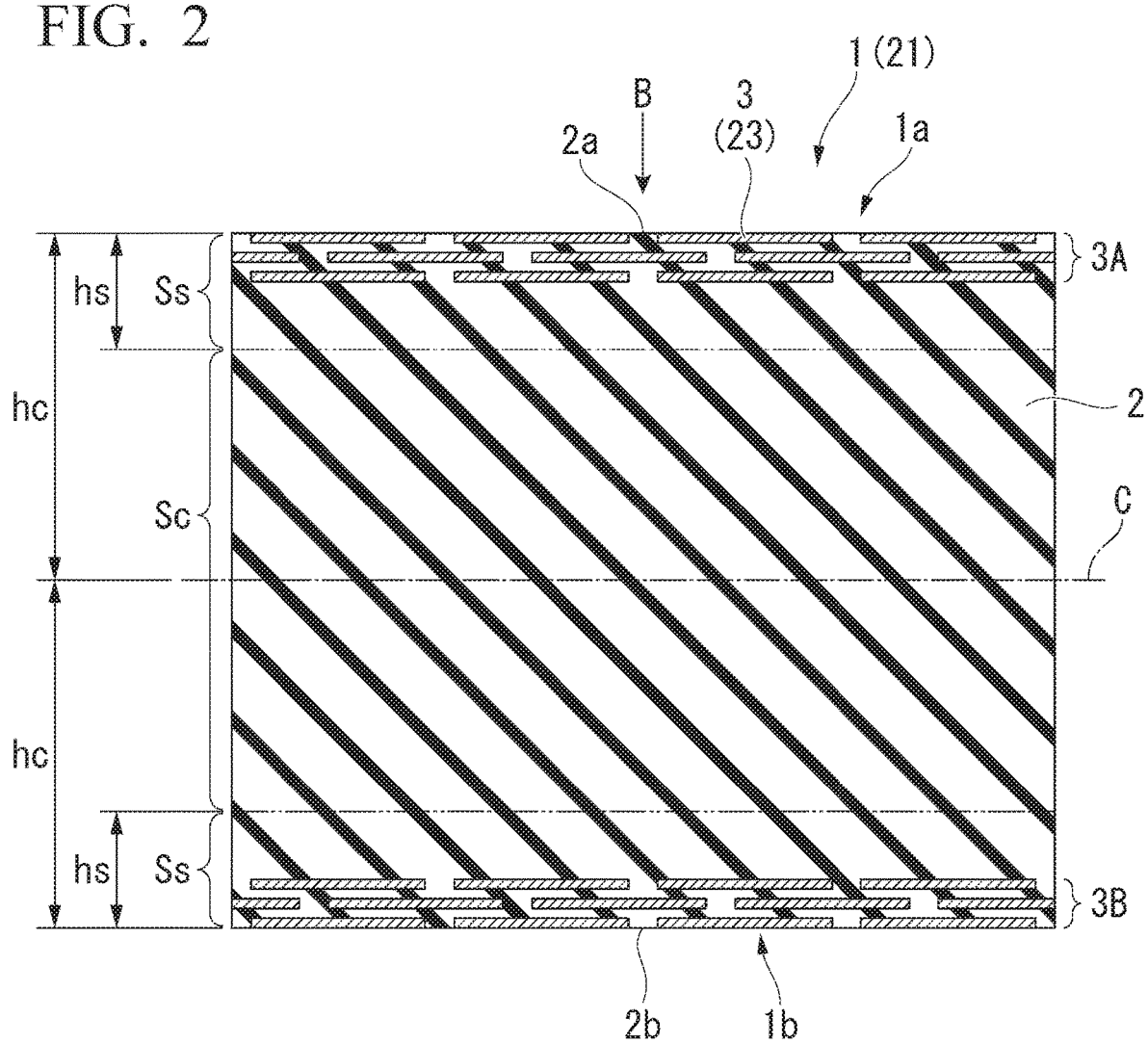
FIG. 2 is a partially enlarged view of the part A in FIG. 1.
Figure 3A:
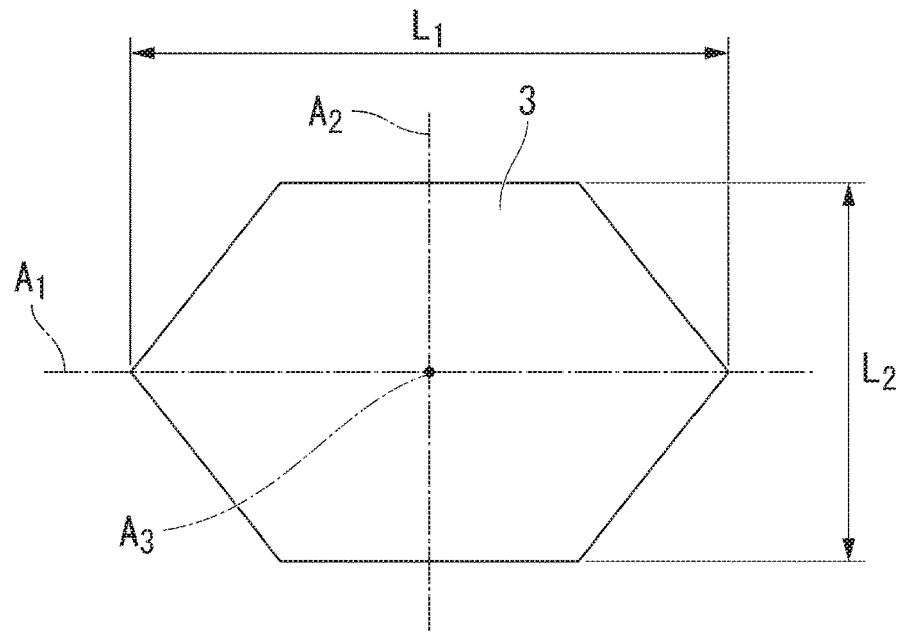
FIG. 3A is a plan view schematically showing an example of a filter of the elastomer molded body for a medical device according to the first embodiment of the present invention.
Figure 3B:
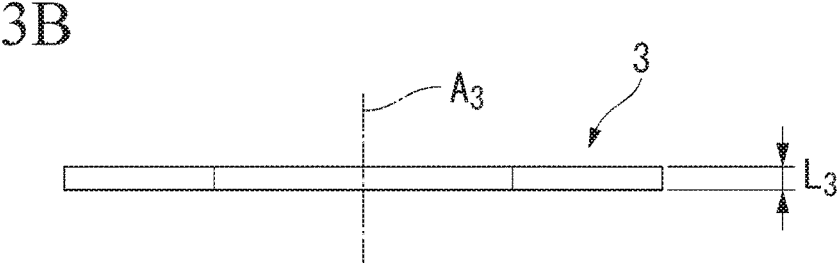
FIG. 3B is a front view schematically showing an example of a filler of the elastomer molded body for a medical device according to the first embodiment of the present invention.
Figure 4:
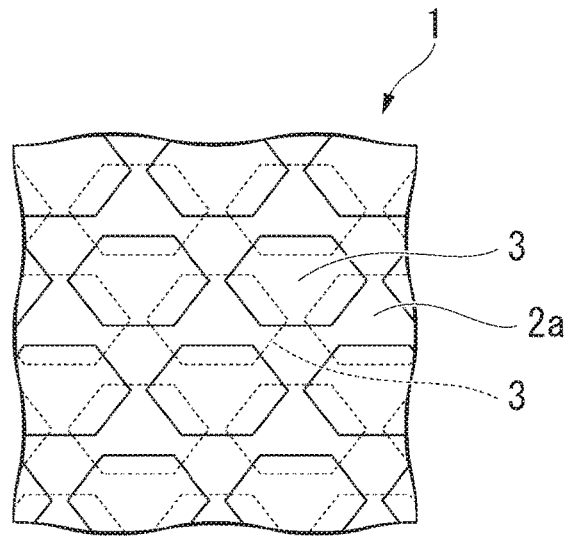
FIG. 4 is a view as seen from a B arrow direction in FIG. 2.

FIG. 1 is a cross-sectional view schematically showing an example of the elastomer molded body for a medical device according to the first embodiment of the present invention. FIG. 2 is a partially enlarged view of the part A in FIG. 1. FIG. 3A is a plan view schematically showing an example of a filler of the elastomer molded body for a medical device according to the first embodiment of the present invention, FIG. 3B is a front view schematically showing an example of a filler of the elastomer molded body for a medical device according to the first embodiment of the present invention. FIG. 4 is a view as seen from a B arrow direction in FIG. 2.

The medical device in which the elastomer molded body for a medical device of the present embodiment is used is not particularly Examples of a medical device in which the elastomer molded body for a medical device of the present embodiment can be used include an endoscope, an endoscopic device, and a surgical treatment instrument.

When the elastomer molded body for a medical device of the present embodiment is used for an endoscopic device, the elastomer molded body for a medical device may be used for, for example, an outer cover of a bending portion or an insertion portion, a fold-proof member for reinforcing a tubular member, a switch button, an outer cover that covers a switch button, an O-ring, and a sealing member.

The shape of the mold for the elastomer molded body for a medical device of the present embodiment is not particularly limited. The shape of the elastomer molded body for a medical device is determined according to the needs of the medical device in which the elastomer molded body for a medical device is used.

Examples of the shape of the elastomer molded body for a medical device include a sheet shape, a rod shape, a ring shape, a tubular shape, a box shape, a cap shape, a coil shape, a bag shape, a band shape, and a block shape. For example, regarding the shape of the elastomer molded body for a medical device, an appropriate three-dimensional shape which cannot be simplified as in the above shapes may be used.

In the following, as shown in FIG. 1, an example in which the shape of the elastomer molded body for a medical device is a cylindrical shape, which is one of tubular shapes, will be described.

A medical device tube 1 as an elastomer molded body for a medical device of the present embodiment is formed in a cylindrical shape. The cross-sectional shapes of an outer circumferential surface 1a (surface of the elastomer molded body) and an inner circumferential surface 1b (surface of the elastomer molded body) of the medical device tube 1 are circular.

The medical device tube 1 may be used as a part of a medical device or the medical device tube 1 itself may be used as a medical device.

For example, the medical device tube 1 may be used as an outer tube of a bending portion or an insertion portion of an endoscopic device. For example, the medical device tube 1 may be used as a part of a medical device or a medical device, in order to form a flow path for an appropriate liquid or gas.

As shown in FIG. 2, the medical device tube 1 includes an elastomer portion 2 and a filler 3.

The elastomer portion 2 constitutes a main part of the medical device tube 1. The elastomer portion 2 is molded along the outer shape of the medical device tube 1 and includes a surface 2a (2b) constituting at least a part of the outer circumferential surface 1a (the inner circumferential surface 1b).

The elastomer portion 2 contains a crosslinked fluorine-based elastomer in which a polymeric fluorine compound is crosslinked. The elastomer portion 2 in which a liquid fluorine based elastomer is dispersed is more preferable. The liquid fluorine-based elastomer can further improve the flexibility of the elastomer portion 2.

The elastomer portion 2 may contain appropriate additive components as necessary. Examples of additive components include a crosslinking gent, a crosslinking aid, a reinforcing agent, a plasticizer, a softening agent, an antioxidant, an acid acceptor, an internal mold release agent, a processing aid, a lubricant, and a curing agent. The additive components contained in the elastomer portion 2 may be of one type or two or more types.

The crosslinked fluorine-based elastomer is not particularly limited as long as it is a crosslinked elastomer having fluorine atoms in its molecule. Specific examples of crosslinked fluorine-based elastomers include crosslinked fluorine rubber and a fluorine-based thermoplastic elastomer.

Examples of a polymeric fluorine compound contained in the crosslinked fluorine rubber include a binary copolymer and a ternary copolymer. The crosslinked fluorine rubber may contain at least one of a binary copolymer and a ternary copolymer.

Examples of binary copolymers include a vinylidene fluoride-hexafluoropropylene copolymer, a tetrafluoroethylene-propylene copolymer, and a tetrafluoroethylene-fluoromethyl vinyl ether copolymer.

Examples of ternary polymers include vinylidene fluoride-hexafluoropropylene-tetrafluoroethylene copolymer, a vinylidene fluoride-propylene-tetrafluoroethylene copolymer, and a vinylidene fluoride-tetrafluoroethylene-perfluoroalkyl vinyl ether copolymer.

More preferably, a vinylidene fluoride-hexafluoropropylene-tetrafluoroethylene copolymer having low crystallinity is contained in the crosslinked fluorine rubber. When a vinylidene fluoride-hexafluoropropylene-tetrafluoroethylene copolymer is contained, the flexibility of the elastomer portion 2 is further improved.

Examples of a polymeric fluorine compound contained in the thermoplastic elastomer include an ethylene-tetrafluoroethylene copolymer, a tetrafluoroethylene-hexafluoropropylene copolymer, polychlorotrifluoroethylene, a tetrafluoroethylene-perfluoroalkyl vinyl ether copolymer, polyvinylidene fluoride, and a chlorotrifluoroethylethylene-ethylene copolymer.

The type of liquid fluorine-based elastomer s not particularly limited as long as it is a fluorine-based elastomer that is a liquid at room temperature and does not have a crosslinking reactive group that forms a crosslinked structure with a crosslinked fluorine-based elastomer. When such a liquid fluorine-based elastomer is dispersed in the elastomer portion 2, the flexibility of the elastomer portion 2 is improved compared to when no liquid fluorine-based elastomer is contained in the elastomer portion 2.

When a liquid fluorine-based elastomer is contained in the elastomer portion 2, more preferably, 10 parts by mass or more and 50 parts by mass or less of the liquid fluorine-based elastomer is contained with respect to 100 parts by mass of the crosslinked fluorine-based elastomer.

When the content of the liquid fluorine-based elastomer is less than 10 parts by mass, there is a possibility of fluidity of a molding material for forming the elastomer portion 2 being reduced. As a result, there is a possibility of the filler 3 to be described below being unlikely to be moved near the surface of the elastomer portion 2.

When the content of the liquid fluorine-based elastomer exceeds 50 parts by mass, in the medical device tube 1, the liquid fluorine-based elastomer may easily bleed on the surface. When the liquid fluorine-based elastomer easily bleeds on the surface, adhesiveness of the surfaces 2a and 2b of the elastomer portion 2 may increase.

Examples of crosslinking agents include ketone peroxides, diacyl peroxides, dialkyl peroxides, peroxyketals, peroxyesters, and percarbonates.

Examples of ketone peroxides include methyl ethyl ketone peroxide and dimethyl ketone peroxide.

Examples of diacyl peroxides include dibenzoyl peroxide and benzoyl m-methyl benzoyl peroxide.

Examples of dialkyl peroxides include 2,5-dimethyl-2,5-bis(tert-butylperoxy)hexane and 2,5-dimethyl-2,5-bis(tert-butylperoxy)3-hexyne.

Examples of peroxyketals include 1,1-bis(tert-hexylperoxy)cyclohexane and 1,1-bis(tert-butylperoxy)cyclohexane.

Examples of peroxyesters include 2,5-dimethyl-2,5-bis (benzoylperoxy)3-hexyne, and tert-hexylperoxybenzoate.

Examples of percarbonates include diisopropyl peroxy dicarbonate, and bis(4-tert-butylcyclohexyl)peroxy carbonate.

Among the crosslinking agents described above, 2,5-dimethyl-2,5-bis(tert-butylperoxy)hexane contained in the elastomer portion 2 is particularly preferable. In this case, a crosslinking rate more suitable for molding the medical device tube 1 is obtained. Therefore, in molding of the medical device tube 1, defects of molding such as a short shot and a burning fault are reduced.

When a crosslinking agent is contained in the elastomer portion 2, more preferably, 1.5 parts by mass or more and 5 parts by mass or less of the crosslinking agent is contained with respect to 100 parts by mass of the crosslinked fluorine-based elastomer.

When the content of the crosslinking agent is less than 1.5 parts by mass, uncrosslinked portions may be generated. As a result, the elastomer portion 2 may break at the uncrosslinked portions.

When the content of the crosslinking agent exceeds 5 parts by mass, unreacted material may remain. As a result, appearance defects such as bleeding may occur.

Examples of crosslinking aids include an allylic compound and an acrylic compound.

Examples of allylic compounds include triallyl isocyanurate, trimethallyl isocyanurate, and triallyl cyanurate.

Examples of acrylic compounds include trimethylolpropane trimethacrylate, 1,9-nonanediol dimethacrylate, tricyclodecane dimethanol dimethacrylate, and polyethylene glycol dimethacrylate.

Among the crosslinking aids described above, triallyl isocyanurate contained in the elastomer portion 2 is more preferable.

In this case, since the crosslinking efficiency is improved by a trifunctional allyl group of triallyl isocyanurate, the tear strength of the elastomer portion 2 is further improved. In addition, when a triazine ring of triallyl isocyanurate of the elastomer portion 2 is introduced, the heat resistance, hydrolysis resistance, and weather resistance of the elastomer portion 2 are improved.

When a crosslinking aid is contained in the elastomer portion more preferably, greater than 0 parts by mass and 10 parts by mass or less of the crosslinking aid is contained with respect to 100 parts by mass of the cross linked fluorine-based elastomer.

When the crosslinking aid is contained, since the crosslinking efficiency increases, mechanical properties of the elastomer portion 2 are further improved.

When the content of the crosslinking agent exceeds 10 parts by mass, bleeding may occur due to the crosslinking aid which is not used for a crosslinking reaction. As a result, appearance defects of the medical device tube 1 may occur.

Examples of reinforcing agents include thermal black, furnace black, channel black, silica, barium sulfate, titanium oxide, calcium carbonate, calcium silicate, magnesium silicate, aluminum silicate, potassium titanate, clay, wollastonite, aluminum hydroxide, magnesium hydroxide, kaolin, montmorillonite, glass fillers, glass fibers, carbon nanotubes, and cellulose nanofibers.

The reinforcing agent added to the elastomer portion 2 may be of one type or a plurality of types.

Among the reinforcing agents described above, an agent including thermal black is more preferable. In this case, the tensile strength of the elastomer portion 2 is further improved.

When a reinforcing agent is contained in the elastomer portion 2, more preferably, greater than 0 parts by mass and 50 parts by mass of the reinforcing agent is contained with respect to 100 parts by mass of the crosslinked fluorine-based elastomer.

When the reinforcing agent is contained, mechanical properties of the elastomer portion 2 are further improved.

When the content of the reinforcing agent exceeds 50 parts by mass, the flexibility of the elastomer portion 2 may be lowered.

As shown in FIG. 2, the filler 3 is unevenly distributed in a surface layer part Ss of the elastomer portion 2. In addition, the filler 3 is oriented, in a direction along the outer circumferential surface 1a (the inner circumferential surface 1b) in a vicinity 3A and a vicinity 3B of the outer circumferential surface 1a (the inner circumferential surface 1b) of the medical device tube 1 which is at least a surface of the elastomer molded body.

Here, the surface layer art Ss of the elastomer portion 2 is defined as follows. A distance from the surface 2a (2b) of the elastomer portion 2 to a layer thickness center plane C which is the center of the elastomer portion 2 in the layer thickness direction represented as hc. In this case, the surface layer part Ss of the elastomer portion 2 is defined as being in a distance range of hs (=0.01·hc) from the surface 2a (2b) of the elastomer portion 2.

In the following, an area excluding a range overlapping the surface layer part Ss in the elastomer portion 2 is referred to as a center portion Sc of the elastomer portion 2.

When it is stated that the filler 3 is "unevenly distributed in the surface layer a Ss," it means that an amount of filler 3 in the surface layer part Ss is larger than an amount of the filler 3 in the center portion Sc.

For example, in the medical device tube 1, 0% or more and less than 40% of the filler 3 may be distributed in the center portion Sc, and 60% or more and 100% or less thereof may be distributed in the surface layer part Ss. In the medical device tube 1, more preferably, 0% or more and less than 25% of the filler 3 may be distributed in the center portion Sc, and 75% or more and 100% or less thereof may be distributed in the surface layer part Ss.

In the present the "vicinity" of the outer circumferential surface 1a (the inner circumferential surface 1b) is defined as a distance range of 0.5·hs from outer circumferential surface 1a (the inner circumferential surface 1b).

More preferably, the filler 3 is oriented in a direction along the outer circumferential surface 1a (the inner circumferential surface 1b) in the entire surface layer part Ss.

An amount of the filler 3 distributed in the center portion Sc and the surface layer part Ss can be measured by, for example, counting particles of the filler 3 in an appropriate cross section of the medical device tube 1.

When the elastomer molded body for a medical device is formed in a clumped shape different from a cylindrical shape, such as a rod shape, a block shape, or the like, a boundary between the surface layer part and the center portion s defined with the distance hs obtained in the same manner as above based on a distance between the surface of the elastomer portion and the center of the elastomer portion in place of the distance hc. Here, the surface of the elastomer molded body for a medical device be selected among surfaces in which the sliding properties are preferably improved. For example, the surface may be a surface used for sliding in the elastomer molded body for a medical device.

The filler 3 has an appropriate shape that can be oriented in a direction along the outer circumferential surface 1a (the inner circumferential surface 1b) of the medical device tube 1.

In the present embodiment, each of the particles of the filler 3 has a shape having an aspect ratio which is a ratio of a dimension in the long axis direction to a dimension in the short axis direction of 5 or more and a specific surface area of 3 $m^2/g$ or more and 10 $m^2/g$ or less.

A more preferable range of the aspect ratio is 10 or more. Here, the aspect ratio may be 100 or less, and more preferably 50 or less.

Examples of such a shape include a flat shape, a curved plate shape, a rod shape, and a needle-like shape.

For example, as shown in FIG. 3A and FIG. 3B, when the filler 3 is composed of plate-like particles, a major diameter $L_1$, a minor diameter $L_2$, and a plate thickness $L_3$ (here, $L_1 \geq L_2 > L_3$) are determined as representative dimensions of the filler 3.

The major diameter $L_1$ is defined as a maximum outer shape dimension when viewed in a direction along an axis $A_3$ that extends in a direction in which the outer shape of the filler 3 looks to be largest. The major diameter $L_1$ is a maximum outer shape dimension in the filler 3. The major diameter $L_1$ is a dimension in the long axis direction that defines the above aspect ratio in the filler 3. An axis $A_1$ that is orthogonal to the axis $A_3$ and extends in a direction in which the major diameter $L_1$ is measured is an axis that represents the long axis direction in a three-dimensional shape of the filler 3.

In addition, the axis $A_1$ is also an axis that defines the long axis direction of the outer shape in plan view when viewed in a direction along the axis $A_3$.

The minor diameter $L_2$ is defined as a minimum outer shape dimension when viewed in a direction along the axis $A_3$. An axis $A_2$ that is orthogonal to the axis $A_3$ and extends in a direction in which the minor diameter $L_2$ is measured is an axis that represents the short axis direction of the cotter shape in plan view.

The plate thickness $L_3$ is a maximum outer shape dimension of the filler 3 measured in a direction along the axis $A_3$. The plate thickness $L_3$ is a dimension in the short axis direction that defines the above aspect ratio in the filler 3.

The aspect ratio of the filler 3 shown in FIG. 3A and FIG. 3B is defined as $L_1/L_3$.

As an example, the shape of the filler 3 in plan view shown in FIG. 3A and FIG. 3B is a hexagonal plate-like particle. However, the shape of the filler 3 in plan view is not limited to a hexagon. For example, the shape of the filler 3 in plan view may be a convex polygon, a concave polygon, an ellipse, or an amorphous shape in which various irregular shapes and bending shapes are combined other than a hexagon.

A ratio between the major diameter $L_1$ and the minor diameter $L_2$ in the filler 3 is not particularly limited as long as the aspect ratio between the major diameter $L_1$ and the plate thickness $L_3$ is within the above range. For example, the major diameter $L_1$ and the minor diameter $L_2$ may be the same.

FIG. 3B shows an example in which the plate thickness of the filler 3 is constant. However, the plate thickness of the filler 3 may change continuously or stepwise depending on the location. For example, the plate thickness of the filler 3 may be the largest at the center portion of the filler 3 in plan view and may decrease toward the circumferential portion of the filler 3 in plan view.

In the following, an example in which the filler 3 is a plate-like particle will be described.

When the filler 3 is a plate-like particle, the phrase "oriented in a direction along the outer circumferential surface 1a (the inner circumferential surface 1b)" means that the axis $A_3$ is in a direction normal to the outer circumferential surface 1a (the inner circumferential surface 1b) (substantially parallel to the normal). In the present embodiment, a direction normal to the outer circumferential surface 1a (the inner circumferential surface 1b) matches a radial direction of the medical device tube 1 and a layer thickness direction of a layered part between the outer circumferential surface 1a and the inner circumferential surface 1b.

Therefore, as schematically shown in FIG. 4, when the filler 3 is viewed in a radial direction of the medical device tube 1, the filler 3 is disposed in a direction in which it looks substantially the same as the outer shape in plan view.

In the filler 3 exposed to the surface 2a, an area of the maximum outer shape of the filler 3 in plan view can also be exposed. However, depending on the surface shape of the filler 3 or a degree of orientation, the exposed area of the filler 3 may be a smaller area than the maximum outer shape in plan view.

FIG. 4 is a schematic view, and in FIG. 4, an example in which the outer shapes of the filler 3 in plan view and the size of the outer shapes in plan view are the same is shown. However, in the filler 3, particles with various shapes and sizes that can be obtained in the above ranges of the aspect ratio and specific surface area may be mixed.

In addition, in FIG. 4, the particles of the filler 3 in the long axis direction in plan view are shown to be aligned with the axial direction (in the left to right direction in FIG. 4) of the medical device tube 1. However, the long axis direction of the particles of the filler plan view may be a direction intersecting the axial direction of the medical device tube 1.

As shown in FIG. 2, the plurality of fillers 3 embedded inside the elastomer portion 2 are laminated on one another in the radial direction of the medical device tube 1. FIG. 2 is a schematic view, and in FIG. 2, an example in which the fillers 3 are laminated with a part of the elastomer portion 2 therebetween is shown. In this manner, when the fillers 3 are laminated with a part f the elastomer portion 2 therebetween, the flexibility of the medical device tube 1 is maintained even if the fillers 3 are dense.

However, if the flexibility of the medical device tube 1 is not impaired, the fillers 3 may be laminated on one another without part of the elastomer portion 2 therebetween.

More preferably, distribution of the fillers 3 when viewed in a radial direction of the medical device tube 1 is substantially uniform in the axial direction and the circumferential direction.

The material of the filler 3 is not particularly limited as long as the material can improve the slipperiness on the surface of the medical device tube 1 when it has the above shape and is exposed from the surfaces 2a and 2b.

Examples of a material of the filler 3 include alumina, mica, diatomaceous earth, talc, clay, boehmite.

Among the above-described materials, alumina is more preferably used. Since alumina has a robust crystal structure, perforation resistance of the medical device tube 1 is particularly favorable.

More preferably, 0.2 parts by mass or more and 1 part by mass or less of the fillers 3 are contained with respect to 100 parts by mass of the crosslinked fluorine-based elastomer.

When the content of the fillers 3 is less than 0.2 parts by mass, since an amount of the fillers 3 distributed, in the vicinity 3A of the outer circumferential surface 1a and the vicinity 3B of the inner circumferential surface 1b is too small, an amount of the fillers 3 exposed to the surfaces 2a and 2b may be too small. As a result, the slipperiness on the outer circumferential surface 1a and the inner circumferential surface 1b may deteriorate.

When the content of the fillers 3 exceeds 1 part by mass, the rigidity of the medical device tube 1 may be excessive. As a result, flexibility of the medical device tube 1 may be lowered.

The medical device tube 1 described above is manufactured according to a method of manufacturing of an elastomer molded body for a medical device according to the present embodiment to be described below.

Figure 5:
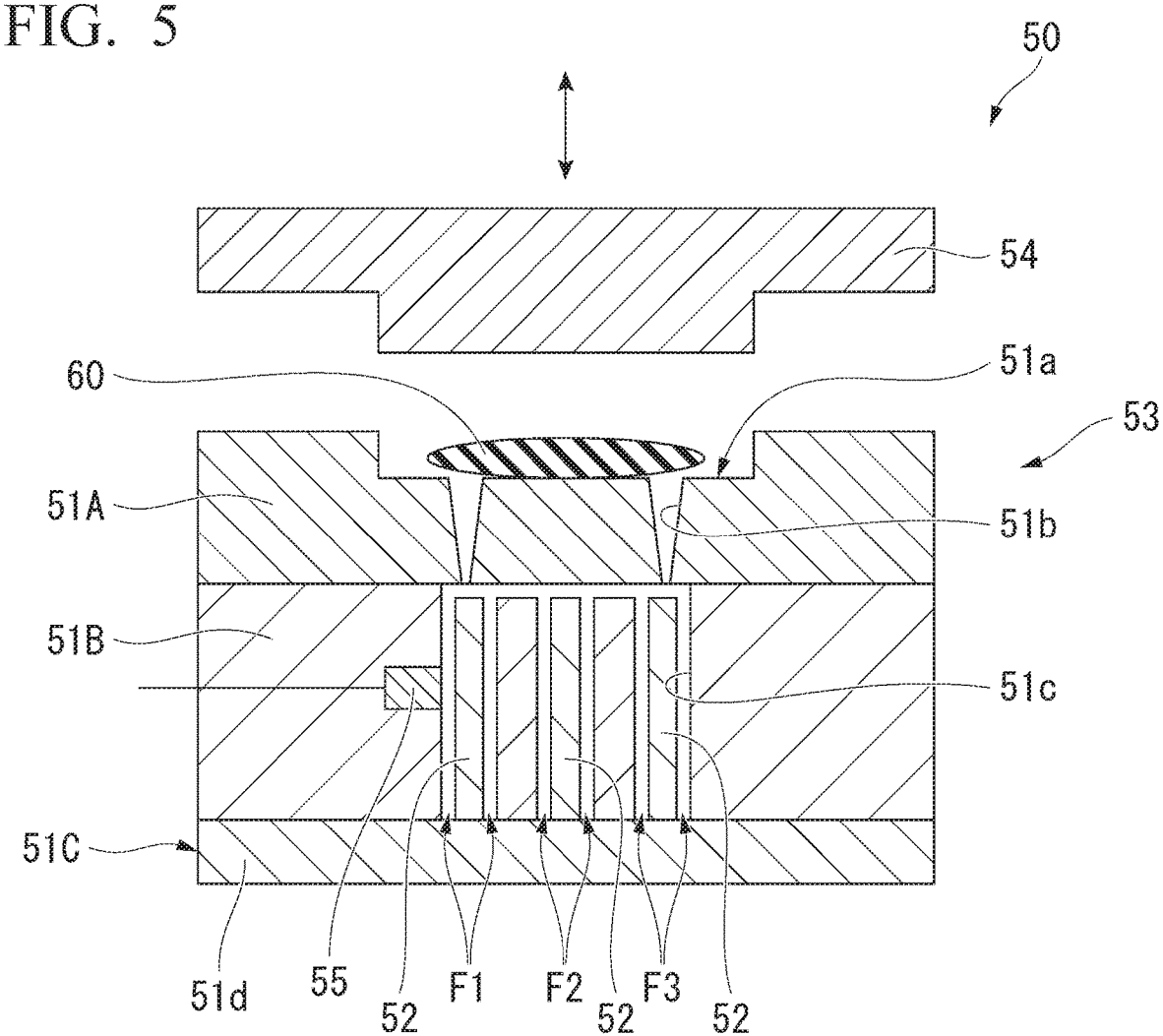
FIG. 5 is a schematic view showing an example of a mold used in a method of manufacturing of an elastomer molded body for a medical device according to the first embodiment of the present invention.
Figure 6:
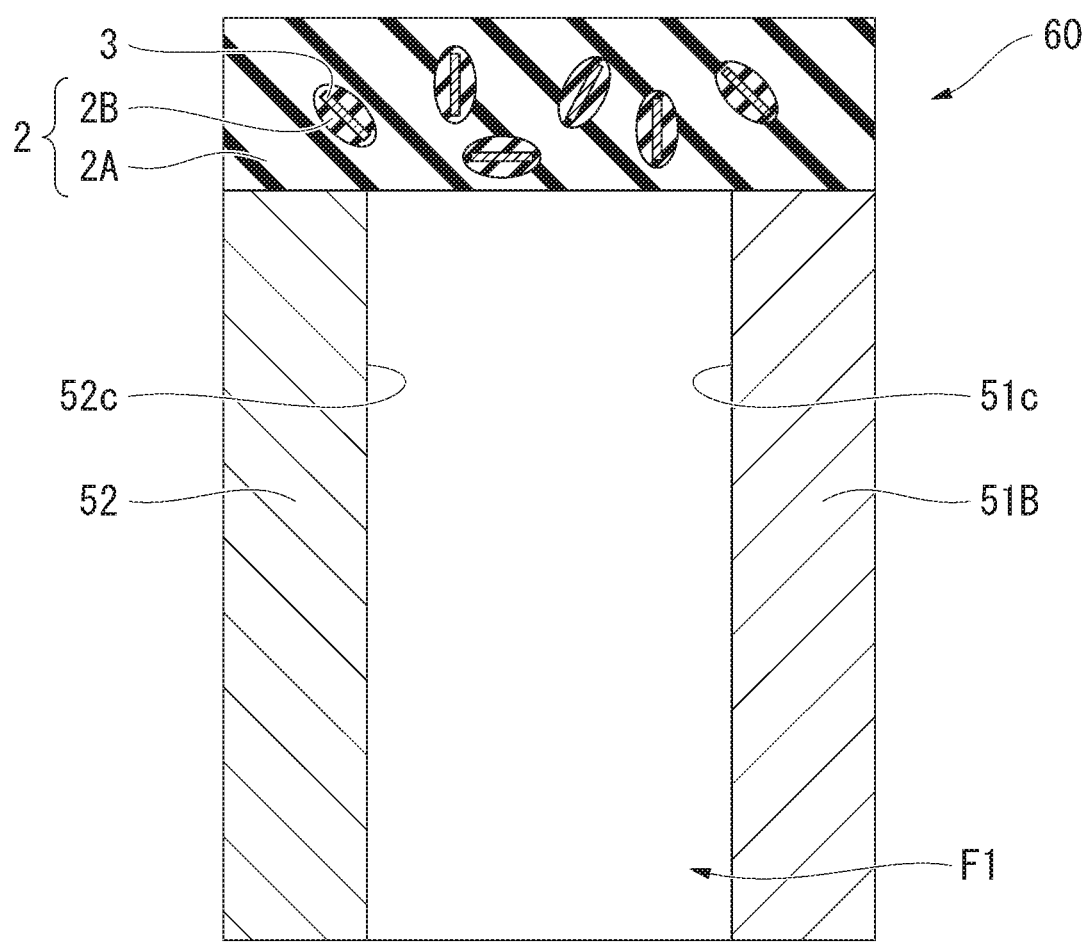
FIG. 6 is a process illustration diagram of the method of manufacturing of an elastomer molded body for a medical device according to the first embodiment of the present invention.
Figure 7:
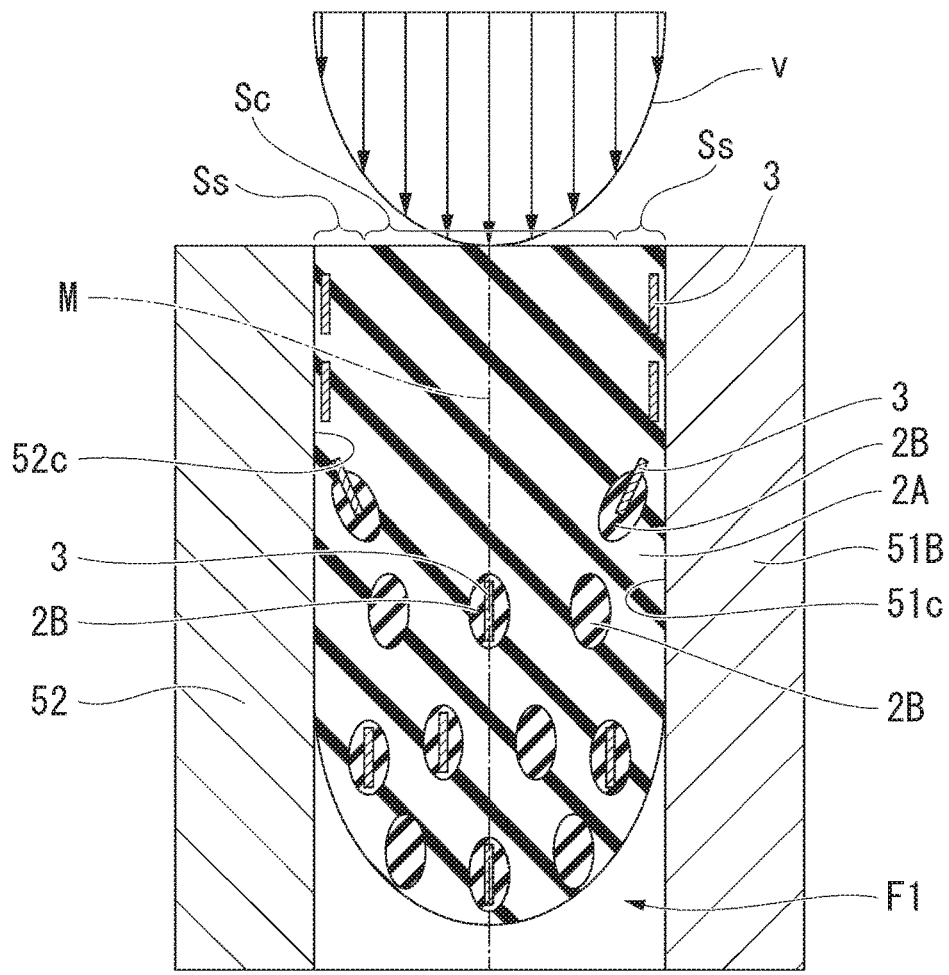
FIG. 7 is a process illustration diagram of the method of manufacturing of an elastomer molded body for a medical device according to the first embodiment of the present invention.

FIG. 5 is a schematic view showing an example of a mold used in a method of manufacturing of an elastomer molded body for a medical device according to the first embodiment of the present invention. FIGS. 6 and 7 are process illustration diagrams of the method of manufacturing of an elastomer folded body for a medical device according to the first embodiment of the present invention.

The method of manufacturing of an elastomer molded body for a medical device according to the present embodiment includes a kneading process and a molding process.

The kneading process includes kneading an elastomer molding material containing an uncrosslinked fluorine-based elastomer and fillers 3 to form a kneaded material.

The uncrosslinked fluorine-based elastomer includes at least a raw material component for forming the above crosslinked fluorine-based elastomer. When the above liquid fluorine-based elastomer is contained in the elastomer portion 2, the liquid fluorine-based elastomer is also contained in the uncrosslinked fluorine-based elastomer in the kneaded material.

The above additive component may be contained in the elastomer molding material as necessary.

Regarding the kneading device, for example, a kneading machine such as an open roller a kneader or a Banbury mixer may be used.

When the elastomer molding material is kneaded by a kneading device, a kneaded material is formed. In the kneaded material, components of the elastomer molding material are substantially uniformly dispersed.

After the kneading process is performed, the molding process is performed. The molding process includes injecting a kneaded material into a molding space of a mold at a flow rate of 30 mm/min or more and 150 mm/min or less to mold the kneaded material in the mold.

The molding process is performed by an appropriate molding method through which a kneaded material can be injected into a molding space at the above flow rate. Regarding the molding method, for example, transfer molding or injection molding is used.

In order to perform such a molding method, a transfer molding machine or an injection molding machine on which a mold for forming the shape of the medical device tube 1 is mounted is used.

In the following, an example in which transfer molding is performed will be described.

FIG. 5 shows a molding apparatus 50 for manufacturing of the medical device tube 1 according to transfer molding.

The molding apparatus 50 includes a mold 53 and a pressing portion 54. Although not shown, the molding apparatus 50 includes a control unit configured to control device operations including an operation of the pressing portion 54.

The mold 53 includes an upper mold 51A, an intermediate mold 51B, a lower mold 51C, and a flow rate sensor 55.

The upper mold 51A has a pot portion 51a that is a hole in which a kneaded material 60 is disposed.

The intermediate mold 51B has a molding surface 51c that forms the outer shape of a molded body, and constitutes a cavity together with the upper mold 51A. In the present embodiment, the molding surface 51c is composed of a columnar hole for transferring the shape of the outer circumferential surface 1a of the medical device tube 1.

In the example shown in FIG. 5, the mold 53 has a multi-cavity in which the medical device tube 1 is molded at three points in the shown cross section.

A gate 51b for transferring the kneaded material 60 into a molding space to be described below is provided between the pot portion 51a and the cavity.

The gate 51b has a diameter that is reduced from the pot portion 51a toward the cavity and thus accelerates the kneaded material 60 that is transferred through the gate 51b.

The lower mold 51C has a configuration in which a core pin 52 that can be inserted into the molding surface 51c stands upward on a plate 51d in contact with the intermediate mold 51B. In the present embodiment, the core pin 52 is composed of a columnar member having a molding surface 52c for transferring the shape of the inner circumferential surface 1b of the medical device tube 1.

When the mold 53 is blocked as shown in FIG. 5, cylindrical molding spaces F1, F2, and F3 corresponding to the outer shape of the medical device tube 1 are formed between the molding surface 51c in the intermediate mold 51B and the molding surface 52c of the core pin 52 inserted into a hole in the molding surface 51c.

The flow rate sensor 55 is a device unit configured to measure a flow rate of the kneaded material 60. A value of the flow rate measured by the flow rate sensor 55 is used by a control unit (not shown) to control an operation of the pressing portion 54 to be described below. In FIG. 5, an example in which the flow rate sensor 55 measures a flow rate in the molding space F1 is shown. However, a plurality of flow rate sensors 55 may be provided so that flow rates in other molding spaces can be measured. In addition, a plurality of flow rate sensors 55 may be disposed in a flow direction in one molding space.

The pressing portion 54 is a device unit that pressurizes the kneaded material 60 disposed in the pot portion 51a toward the gate 51b and thus transfers the kneaded material 60 into the molding spaces F1, F2, and F3.

The pressing portion 54 can pressurize the kneaded material 60 so that a flow rate of the kneaded material 60 that flows through the molding spaces F1, F2, and F3 becomes 30 mm/min or more and 150 mm/min or less.

The operation of the pressing portion 54 is controlled by a control unit (not shown) based on a flow rate that is detected by the flow rate sensor 55.

In order to mold the kneaded material 60 using the molding apparatus 50, an amount be kneaded material 60 necessary for molding which has been weighed out is placed on the pot portion 51a.

The control unit of the molding apparatus 50 moves the pressing portion 54 toward the pot portion 51a. The kneaded material 60 is transferred into the molding spaces F1, F2, and F3 through the gate 51b due to a pressurizing from the pressing portion 54.

The molding spaces F1, F2, and F3 are cylindrical spaces that extend in the vertical direction in FIG. 5, in correspondence with the medical device tube 1. Therefore, the kneaded material 60 flowing from the gate 51b is pushed in the longitudinal direction of the molding spaces F1, F2, and F3.

In this case, when a pressurizing force of the pressing portion 54 is controlled by the control unit (not shown), a flow rate of the kneaded material 60 that flows through the molding spaces F1, F2, and F3 becomes a flow rate selected in advance from a range of 30 mm/min or more and 150 mm/min or less.

When the kneaded material 60 is filled into the molding spaces F1, F2, and F3, pressurization by the pressing portion 54 is stopped.

Hereafter, in order to crosslink a raw material of the crosslinked fluorine-based elastomer contained in the kneaded material 60, the temperature of the mold 53 is raised to a crosslinking temperature. Thereby, crosslinking of the uncrosslinked fluorine-based elastomer that is crosslinkable proceeds to form a crosslinked fluorine-based elastomer.

After desired crosslinking is completed, the molded body is demolded. Hereafter, as necessary, the molded body is additionally heated in order to perform secondary crosslinking, and cut into an appropriate dimension.

In this manner, the medical device tube 1 is manufactured.

Here, a principle by which the fillers 3 are oriented on the surface layer part Ss according to the present method of manufacturing will be described. Since the configurations of the molding spaces are the same, an example of the molding space F1 will be described below.

FIG. 6 schematically shows an appearance of the kneaded material 60 that has reached an inlet portion of the molding space F1. In the following, first, an example in which an uncrosslinked fluorine-based elastomer 2A and a liquid fluorine-based elastomer 29 as raw materials of the crosslinked fluorine-based elastomer are contained in the kneaded material 60 will be described.

Since the liquid fluorine-based elastomer 2B is a liquid at room temperature, it has a function of reducing the flexibility and viscosity of the entire kneaded material 60. In addition, the liquid fluorine-based elastomer 29 is mixed with the fillers 3 according to kneading. Specifically, while the liquid fluorine-based elastomer 2B adheres to the fillers 3 in the kneaded material 60 or contains the fillers 3, the fillers 3 are dispersed in the liquid fluorine-based elastomer 2B. Thereby, the liquid fluorine-based elastomer 2B is interposed between the filler 3 and the uncrosslinked fluorine-based elastomer 2A. Therefore, the liquid fluorine-based elastomer 2B has a function of improving the mobility of the fillers 3 in the kneaded material 60.

In the following, in the kneaded material 60, the filler 3 to which the liquid fluorine-based elastomer 2B adheres or which is dispersed in the liquid fluorine-based elastomer 2B will be referred to as "the filler 3 with the liquid fluorine-based elastomer 2B."

As shown in FIG. 7, when the kneaded material 60 is transferred to the molding space F1, the kneaded material 60 is pushed into the molding space F1 in the longitudinal direction in an area with a fixed width between the molding surfaces 51c and 52c, and flows downward from the upper side in FIG. 7 as a laminar flow. Since the kneaded material 60 is a viscous fluid, a velocity distribution in the kneaded material 60 is determined according to Newton's viscosity law. Specifically, as the velocity distribution v schematically shown in FIG. 7, a velocity distribution in which a flow rate of the molding surfaces 51c and 52c as wall surfaces is 0, and the flow rate becomes a maximum on an intermediate surface M between the molding surfaces 51c and 52c is formed.

Therefore, a component having high fluidity flows in advance along the intermediate surface M on the molding space F1. On the other hand, a component having low fluidity remains in the vicinity of the molding surfaces 51c and 52c. Therefore, in the cross section of the flow path in the molding space F1, a component having low fluidity is likely to be distributed in the surface layer part of the molded body. For example, in the kneaded material 60, since the liquid fluorine-based elastomer 2B is a component having the highest fluidity, it tends to accumulate near the intermediate surface M and flow in advance. In be flow path through which the preceding liquid fluorine-based elastomer 2B flows, other following components easily flow therethrough.

The uncrosslinked fluorine-based elastomer 2A having low fluidity adheres to the vicinity of the molding surfaces 51c and 52c, and is molded into the shape of the molding surfaces 51c and 52c.

Since the filler 3 has a higher aspect ratio than a spherical shape, it is a component having low fluidity as a single substance. However, since the fillers the liquid fluorine-based elastomer 2B have improved fluidity, they move together with the liquid fluorine-based elastomer 2B to a certain extent.

However, when the fillers 3 with the liquid fluorine-based elastomer 2B move to an area with a low flow rate, the fillers 3 are left behind from the liquid fluorine-based elastomer 2B having higher fluidity.

The fillers 3 left behind are pressed toward the molding surface 51c (52c) due to a slow flow of the uncrosslinked fluorine-based elastomer 2A having high viscosity. In addition, they are oriented in a direction in which the resistance is further reduced according to a similar flow. Specifically, the fillers 3 are oriented along the molding surfaces 51c and 52c.

In this manner, in the kneaded material 60 that flows through the molding space F1, the liquid fluorine-based elastomer 2B easily accumulates an area near the intermediate surface M, and the uncrosslinked fluorine-based elastomer 2A and the fillers 3 easily accumulate in n area near the molding surfaces 51c and 52c. In addition, since the fillers 3 in the vicinity of the molding surfaces 51c and 52c are oriented long the molding surfaces 51c and 52c, a layered part having a high density of the fillers 3 is formed in the vicinity of the molding surfaces 51e and 52c.

Thus, a structure in which the fillers 3 are unevenly distributed in the surface layer part Ss as shown in FIG. 2 is formed.

When crosslinking is caused to proceed in such a state, since disposition of the fillers 3 is fixed, the medical device tube 1 having the same configuration as an internal structure of the kneaded material 60 is manufactured.

An example in which the liquid fluorine-based elastomer 2B is contained in the kneaded material 60 has been described above. However, even if the kneaded material 60 does not contain the liquid fluorine-based elastomer 2B, since the fluidity of each component in the kneaded material 60 is not uniform, a component having high fluidity and a component having low fluidity are contained in the kneaded material 60. Therefore, when a flow rate is appropriately set according to the viscosity of the kneaded material 60, the fillers 3 can be distributed similarly.

According to the medical device tube 1 as the elastomer molded body for a medical device of the present embodiment, since some of the fillers 3 are exposed to the outer circumferential surface 1a and the inner circumferential surface 1b, the slipperiness on the surface of the medical device tube 1 is improved compared to when only the elastomer portion 2 having adhesiveness is exposed to the outer circumferential surface 1a and the inner circumferential surface 1b.

In addition, since the fillers 3 on the surface layer part Ss are oriented along the outer circumferential surface 1a (the inner circumferential surface 1b), the inner elastomer portion 2 is covered in a substantially layer form with a large number of fillers 3. Therefore, bleeding from the inside is reduced. In addition, since the fillers 3 have resistance to an external force from the outside, the mechanical resistance of the medical device tube 1 is improved. Specifically, the strength, perforation strength, tear strength, and hardness of the medical device tube 1 are improved.

In the medical device tube 1, in the center portion Sc that occupies a wider area than the surface layer part Ss, a large amount of the liquid fluorine-based elastomer 2B having high flexibility is dispersed, and an amount of the fillers 3 distributed which causes a reduction in flexibility is small, and thus the flexibility of the medical device tube 1 is maintained.

In this manner, according to the elastomer molded body for a medical device of the present embodiment and the method of manufacturing of an elastomer molded body for a medical device, it is possible to improve the slipperiness on the surface while maintaining flexibility, and it is possible to improve sliding properties with respect to the surface.

In the method of manufacturing of an elastomer molded body for a medical device according to the present embodiment, it is possible to make the fillers 3 be unevenly distributed and oriented on the surface layer part Ss by simply appropriately controlling a flow rate according to molding from the kneaded material 60 in which the fillers 3 are uniformly dispersed. Therefore, in the method of manufacturing of an elastomer molded body for a medical device according to the present embodiment, it is possible to easily manufacture the medical device tube 1 in which distribution and orientation of the fillers 3 are controlled.

[Modified Examples]

Next, an elastomer molded body for a medical device according to a modified example of the present embodiment will be described.

Figure 8:
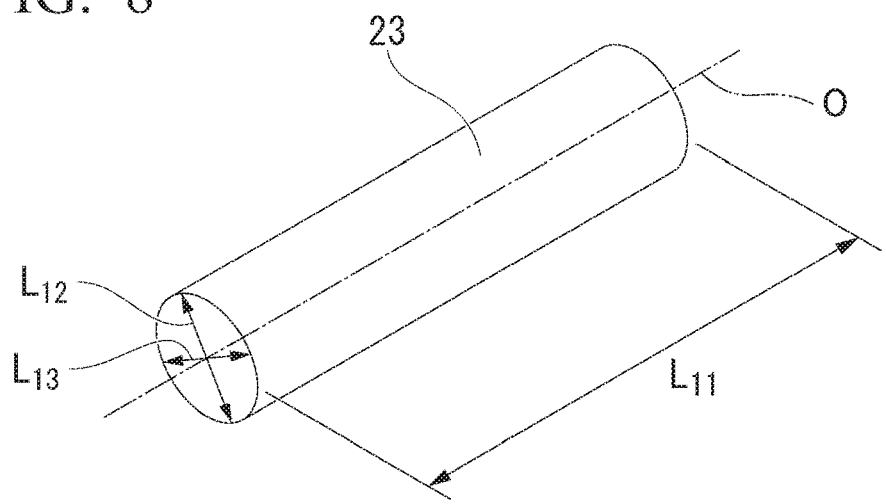
FIG. 8 is a perspective view schematically showing an example of a filler of elastomer molded body for a medical device according to a modified example of the first embodiment of the present invention.

FIG. 8 is a perspective view schematically showing an example of a filler of an elastomer molded body for a medical device according to a modified example of the first embodiment of the present invention.

As shown in FIG. 1, a medical device tube 21 (elastomer molded body for a medical device) according to the present modified example has the same outer shape as the medical device tube 1 according to the first embodiment.

As shown in FIG. 2, the medical device tube 21 according to the present modified example includes a filler 23 in place of the filler 3 of the medical device tube 1 according to the first embodiment.

Differences from the first embodiment will be mainly described below.

The filler 23 in the present modified example is different from the filler 3 in the description of the first embodiment in that the outer shape is a rod shape. For example, regarding the a trial of the filler 23, the same material as the above filler 3 is used.

Even if the filler 23 has a rod shape, like the filler 3 in the first embodiment, an aspect ratio which is a ratio of a dimension in the long axis direction to a dimension the short axis direction is 5 or more and a specific surface area is 3 $m^2/g$ or more and 10 $m^2/g$ or less.

For example, as shown in FIG. 8, the filler 23 is formed of a rod-shaped member in which a length $L_{11}$, a major diameter $L_{12}$, and a minor diameter $L_{13}$ (here, $L_{11} > L_{12} \geq L_{13}$) are determined as representative dimensions.

The length $L_{11}$ is a maximum length along a central axis O (long axis) of the filler 23. The length $L_{11}$ is a maximum outer shape dimension of the filler 3 and a dimension in the long axis direction that defines the above aspect ratio. FIG. 8 is a schematic view, and in FIG. 8, the central axis O is illustrated as a straight line. However, the central axis O may be curved.

The major diameter $L_{12}$ is defined as a maximum outer shape dimension in the cross section perpendicular to the central axis O (hereinafter referred to as a cross section perpendicular to the axis).

The minor diameter $L_{13}$ is defined as a maximum value in the longitudinal direction along the central axis O among minimum outer shape dimensions in the cross section perpendicular to the axis. The minor diameter $L_{13}$ is a dimension in the short axis direction that defines the above aspect ratio.

In FIG. 8, an example in which the cross section perpendicular to the axis of the filler 23 is a circle ($L_{12} = L_{13}$) is shown. However, the cross section perpendicular to the axis of the filler 23 is not limited to a circle. Examples of the shape of the cross section perpendicular to the axis of the filler 23 include an ellipse, a convex polygon, a concave polygon, and an amorphous shape in which various irregular shapes and bending shapes are combined.

In addition, the outer diameter of the cross section perpendicular to the axis of the filler 23 may change gradually or stepwise in the longitudinal direction. For example, the filler 23 may have a needle-like outer shape in which the outer diameter of the cross section perpendicular to the axis is reduced toward one end or both ends.

Since the filler 23 having such a shape has an aspect ratio in the above range, the resistance received from the fluid significantly differs depending on a direction with respect to a flow direction of the kneaded material during molding.

Therefore, according to the same method of manufacturing as in the first embodiment, in the filler 23, the central axis O is oriented in the longitudinal direction of the medical device tube 1 and a direction along the outer circumferential surface 1a (the inner circumferential surface 1b). In addition, like the fillers 3 in the first embodiment, the fillers 23 are unevenly distributed in the surface layer part Ss.

In this manner, in the medical device tube 21 of the present modified example, the fillers 23 are distributed in the same manner as the fillers 3 in the first embodiment. Therefore, the medical device tube 1 can improve the slipperiness on the surface while maintaining flexibility.

Second Embodiment

A medical device according to a second embodiment of the present invention will be described.

Figure 9:
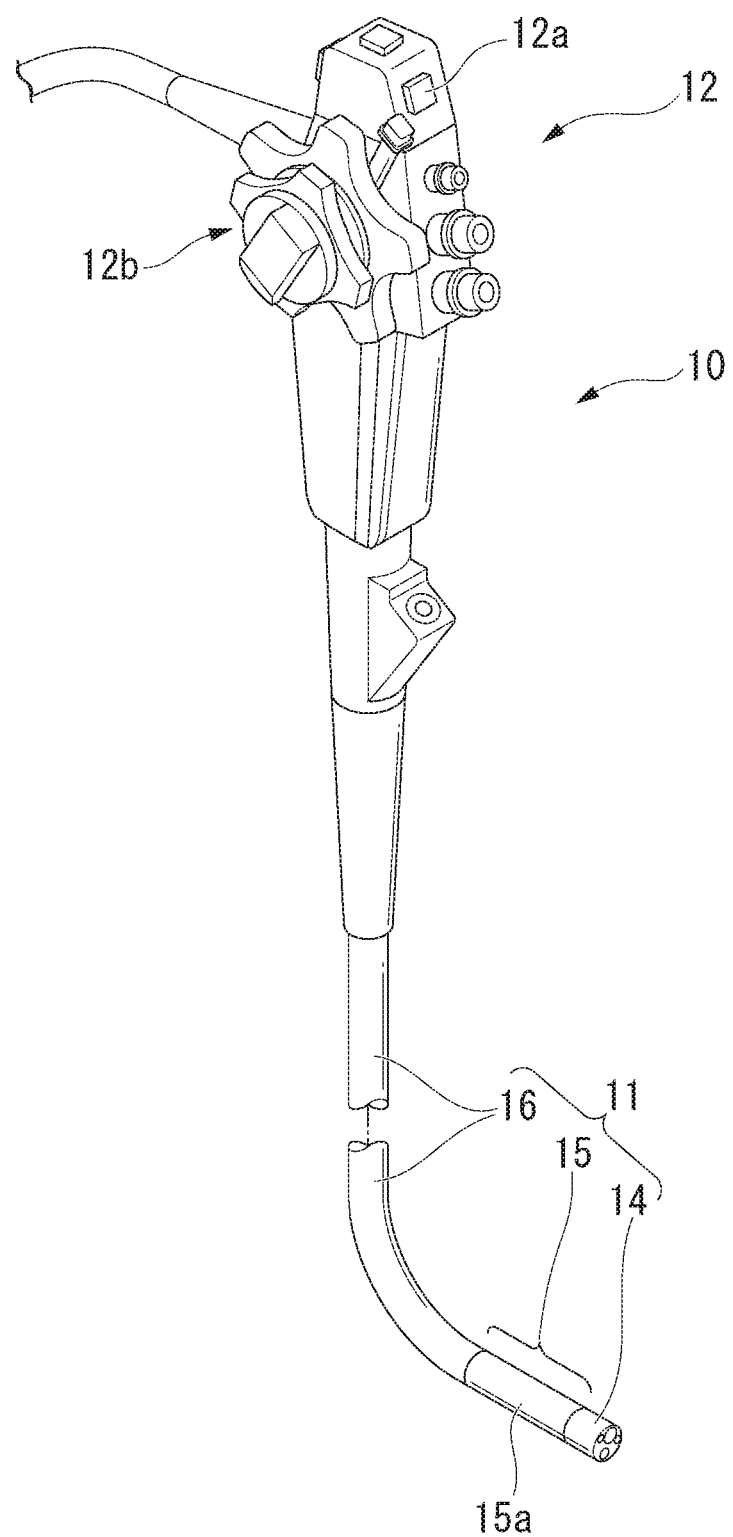
FIG. 9 is a perspective view schematically showing an example of a medical device according to a second embodiment of the present invention.

FIG. 9 is a perspective view schematically showing an example of a medical device according to a second embodiment of the present invention.

As shown in FIG. 9, an endoscope 10 (medical device) according to the present embodiment includes an insertion portion 11 and an operation unit 12

The insertion portion 11 is formed in a flexible tubular shape so that it is inserted into a patient's body. In the insertion portion 11, a distal end portion 14, a bending portion 15, and a flexible tube portion 16 are provided in order from the distal end side in the insertion direction. Although not particularly shown, a endoscopic channel through which a endoscopic device passes may be provided inside the insertion portion 11 in the longitudinal direction.

The distal end portion 14 is a portion that is disposed at the distal end portion of the endoscope 10 and has an end effector as a manipulator. In the present embodiment, for example, the distal end portion 14 internally includes an imaging optical system including an imaging element such as a CCD and an appropriate lens in order to acquire an image of a subject, and has a columnar outer shape.

An imaging window and a lighting window are formed at the distal end of the distal end portion 14. When the insertion portion 11 includes an endoscopic channel, an opening of the endoscopic channel is provided at the distal end of the distal end portion 14.

The bending portion 15 is connected to the proximal end side of the distal end portion 14. The bending portion 15 is bendable in order to change the direction of the distal end portion 14. The bending portion 15 is a tubular part.

For example, the bending portion 15 is configured by connecting a plurality of annular joint rings that are rotatable, and a plurality of angle wires are inserted thereinto.

For example, members such as an electrical wiring connected to an imaging element of the distal end portion 14 and a light guide that extends to a lighting window are accommodated inside the bending portion 15. These members such as an electrical wiring and a light guide are inserted into the flexible tube portion 16 to be described below and extend to the operation unit 12 to be described below.

The bending portion 15 is covered by an outer tube 15a (elastomer molded body for a medical device).

For the outer tube 15a, the same configuration as that of the medical device tube 1 according to the first embodiment is used.

The flexible tube portion 16 is a tubular portion that connects the bending portion 15 to the operation unit 12 to be described below.

The flexible tube portion 16 includes, for example, a spiral tube in which a metal or resin band-like member is spirally wound and a soft covering resin. The covering resin covers the outer periphery of the spiral tube in a tubular shape.

In such a configuration, the flexible tube portion 16 can be bent in an appropriate direction while maintaining a substantially circular cross section.

The material of the covering resin in the flexible tube portion 16 is not particularly limited. For example, regarding the covering resin in the flexible tube portion 16, the same et configuration as that of the medical device tube 1 according to the first embodiment may be used.

A coil sheath is disposed inside the flexible tube portion 16, and angle wires extending from the bending portion 15 to the proximal end side are inserted into the coil sheath. As in the bending portion 15, members such as the above electrical wiring and light guide are inserted into the flexible tube portion 16.

The operation unit 12 is a device unit through which an operator performs an operation of the endoscope 10. Examples of an operation that is performed through the operation unit 12 include an operation of pulling angle wires in order to change a bending amount of the bending portion 15. The operation unit 12 includes, for example, an operation switch 12a and an operation knob 12b.

For example, the operation switch 12a is composed of a switch button

In the operation switch 12a, materials of a button body that is exposed from the operation unit 12 or an outer cover that covers the button body are not particularly limited. Regarding the button body of the operation switch 12a or the outer cover that covers the button body, the elastomer molded body for a medical device according to the first embodiment formed into each shape may be used.

Although not specifically shown, for example, an O-ring, a sealing member, and the like are disposed inside the insertion portion 11. Regarding the O-ring and the sealing member which are not shown, the elastomer molded body for a medical device according to the first embodiment formed into each shape may be used.

For example, the endoscope 10 of the present embodiment has the same configuration as that of the elastomer molded body for a medical device according to the first embodiment such as the outer tube 15a. Therefore, the endoscope 10 has the same function as the elastomer molded body for a medical device according to the first embodiment.

For example, in the outer tube 15a, when the bending portion 15 is bent, since sliding properties with respect to the surface are improved while maintaining flexibility, a bending load can be reduced. For example, since sliding properties between the inner circumferential surface of the outer tube 15a and an internal member such as a spiral tube in contact with the inner circumferential surface become favorable, a sliding load is reduced. For example, since sliding properties between the outer circumferential surface of the outer tube 15a and another medical device that is disposed outside the bending portion 15 become favorable, a sliding load is reduced.

Here, in the description of the embodiments and modified examples, an example in which the elastomer contained, in the elastomer portion 2 of the elastomer molded body for a medical device is only a fluorine-based elastomer has been described. However, an elastomer other than the fluorine-based elastomer may be contained in the elastomer portion 2.

For example, examples of elastomers other than the fluorine-based elastomer include ethylene propylene diene rubber (EPDM), ethylene propylene rubber (EPT), and a silicone elastomer.

In the description of the first embodiment, an example in which a flow rate of the kneaded material 60 during molding is in a range of 30 mm/min or more and 150 min/min or less has been described. However, depending on, for example, a cross-sectional area of a flow path in the molding space, the viscosity of the kneaded material 60, the aspect ratio of the fillers 3, and the like, a flow rate of the kneaded material 60 is not limited to the above-described range. For example, it has been found that the above-described range of the flow rate is particularly suitable when an interval between walls (the molding surfaces 51c and 52c) forming the flow path is 0.2 mm or more and 1.0 mm or less.

For example, a flow rate of the kneaded material 60 during, molding may be 60 mm/min or more and 120 mm/min or less.

EXAMPLES

Examples of the medical device tube 1 according to the first embodiment will be described below together with comparative examples. The following ['Table 1] shows the composition and evaluation results of medical device tubes (in [Table 1], described as a "molded body") of Examples 1 to 4, and Comparative Examples 1 to 6. Here, in [Table 1], reference numerals are not shown.

The following [Table 2] shows the Mooney viscosity of the kneaded materials of Examples 1 to 4, and Comparative Examples 1 to 6, and evaluation results of the distribution and orientation of fillers in evaluation samples to be described below.

TABLE 1

| | COMPOSITION OF MOLDED BODY(PARTS BY MASS) | | | | | |
|---|---|---|---|---|---|---|
| | CROSSLINKED FLUORINE-BASED ELASTOMER | LIQUID FLUORINE-BASED ELASTOMER | CROSSLINKING AGENT | COLORANT | FILLER | TYPE OF FILLER MATERIAL |
| EXAMPLE 1 | 100 | 20 | 2 | 0.2 | 0.5 | ALUMINA |
| EXAMPLE 2 | 100 | 15 | 2 | 0.2 | 1 | ALUMINA |
| EXAMPLE 3 | 100 | 30 | 2 | 0.2 | 0.5 | CLAY |
| EXAMPLE 4 | 100 | 45 | 2 | 0.2 | 0.5 | MICA |
| COMPARATIVE EXAMPLE 1 | 100 | 20 | 2 | 0.2 | 0.5 | ALUMINA |
| COMPARATIVE EXAMPLE 2 | 100 | 20 | 2 | 0.2 | 0.5 | SILICA |
| COMPARATIVE EXAMPLE 3 | 100 | 20 | 2 | 0.2 | 0.1 | ALUMINA |
| COMPARATIVE EXAMPLE 4 | 100 | 20 | 2 | 0.2 | 8 | ALUMINA |
| COMPARATIVE EXAMPLE 5 | 100 | 5 | 2 | 0.2 | 0.5 | ALUMINA |
| COMPARATIVE EXAMPLE 6 | 100 | 60 | 2 | 0.2 | 0.5 | ALUMINA |

| | EVALUATION RESULTS 1 | | | | | |
|---|---|---|---|---|---|---|
| | TYPE OF FILLER SHAPE | COEFFICIENT OF FRICTION | 100% MODULUS (MPa) | PERFORATION STRENGTH (mm) | HARDNESS (SHORE A) | COMPREHENSIVE EVALUATION |
| EXAMPLE 1 | FLAT SHAPE | 0.72 | 3.0 | 100 | 59 | A |
| EXAMPLE 2 | FLAT SHAPE | 0.76 | 4.0 | 110 | 63 | A |
| EXAMPLE 3 | FLAT SHAPE | 0.82 | 3.3 | 80 | 62 | A |
| EXAMPLE 4 | FLAT SHAPE | 0.85 | 3.5 | 80 | 58 | A |
| COMPARATIVE EXAMPLE 1 | NEEDLE-LIKE SHAPE | 1.3 | 3.5 | 60 | 65 | C |
| COMPARATIVE EXAMPLE 2 | SPHERICAL SHAPE | 1.5 | 4.5 | 50 | 60 | C |
| COMPARATIVE EXAMPLE 3 | FLAT SHAPE | 1.2 | 3.1 | 80 | 55 | C |
| COMPARATIVE EXAMPLE 4 | FLAT SHAPE | 1.5 | 5.2 | 130 | 70 | C |
| COMPARATIVE EXAMPLE 5 | FLAT SHAPE | 1.2 | 4.9 | 100 | 69 | C |
| COMPARATIVE EXAMPLE 6 | FLAT SHAPE | 1.5 | 2.6 | 50 | 52 | C |

TABLE 2

| | MOONEY VISCOSITY $ML_{1-10}$ (100° C.) (M) | FILLER SURFACE ABUNDANCE (SURFACE/INSIDE) | QUANTITATIVE VALUE OF Al OR Si (wt %) | |
|---|---|---|---|---|
| | | | SURFACE | INSIDE |
| EXAMPLE 1 | 34 | 3.3 | 1.3 | 0.4 |
| EXAMPLE 2 | 39 | 2.9 | 2.0 | 0.7 |
| EXAMPLE 3 | 32 | 3.3 | 1.0 | 0.3 |
| EXAMPLE 4 | 31 | 3.0 | 1.2 | 0.4 |
| COMPARATIVE EXAMPLE 1 | 33 | 1.4 | 0.7 | 0.5 |
| COMPARATIVE EXAMPLE 2 | 31 | 1.0 | 0.4 | 0.4 |
| COMPARATIVE EXAMPLE 3 | 27 | 1.0 | 0.1 | 0.1 |
| COMPARATIVE EXAMPLE 4 | 45 | 1.1 | 5.3 | 4.9 |
| COMPARATIVE EXAMPLE 5 | 47 | 0.4 | 0.5 | 1.3 |
| COMPARATIVE EXAMPLE 6 | 20 | 0.8 | 0.9 | 1.1 |

Example 1

As shown in the above [Table 1], the composition of the medical device tube 1 of Example 1 included 100 parts by mass of the crosslinked fluorine-based elastomer, 20 parts by mass of the liquid fluorine-based elastomer, 2 parts by mass of the crosslinking agent, 0.2 parts by mass of the colorant, and 0.5 parts by mass of the fillers 3.

Regarding the crosslinked fluorine-based elastomer, a crosslinked fluorine rubber containing a hexafluoropropylene-vinylidene fluoride copolymer, which is a binary copolymer, as a main component was used. Specifically, regarding the crosslinked fluorine-based elastomer, Daiel (registered trademark) G-801 (product name; commercially available from Daikin Industries, Ltd.) was used. A fluorine concentration and Mooney viscosity $ML_{1-10}$ (100° C.) of G-801 were 66% and 66 M, respectively.

Regarding the liquid fluorine-based elastomer, a liquid fluorine rubber containing a hexafluoropropylene-vinylidene fluoride copolymer, which is a binary copolymer, as a main component was used. Specifically, regarding the liquid fluorine-based elastomer, Daiel G-101 (product name; commercially available from Daikin Industries, Ltd.) was used, and a specific gravity and viscosity of G-101 were 1.76 and 3300 P, respectively.

Regarding the crosslinking agent, 2,5-dimethyl-2,5-bis (tert-butylperoxy)hexane as an organic peroxide was used. Specifically, regarding the crosslinking agent, Perhexa (registered trademark) 25B (product name; commercially available from NOF Corporation) was used.

Regarding the colorant, channel black was used. Specifically, Mitsubishi carbon black HCF #2350 (product name; commercially available from Mitsubishi Chemical Corporation) was used. The particle size of HCF #2350 was 15 nm.

Regarding the filler, a flat alumina was used. Specifically, regarding the filler, Serra-sur (registered trademark) BMM (product name; commercially available from Kawai Lime Industry Co., Ltd.) was used. An aspect ratio and average particle size of Serra-sur BMM were 10, and 0.8 μm to 1 μm, respectively. A specific surface area of BMM was 3.4 m$^2$/g, and was in a range of 3 m$^2$/g or more and 10 m$^2$/g or less.

An evaluation sample of the medical device tube 1 of Example 1 was manufactured using the method of manufacturing of an elastomer molded body for a medical device according to the first embodiment described above. The shape of the evaluation sample was a cylindrical tube having an outer diameter of 12 mm, a wall thickness of 0.5 mm, and a length of 100 mm.

In the kneading process, the above crosslinked fluorine rubber raw material, liquid fluorine rubber raw material, crosslinking agent, colorant, and filler were kneaded using an open roller. Thereby, a molding material compound (the kneaded material 60) was produced. As shown in [Table 2], the Mooney viscosity $ML_{1-10}$ (100° C.) of the compound of Example 1 was 34 M.

In the molding process, a compound was filled into a molding space using a transfer molding machine. In this case, a flow rate of the compound was 120 mm/min.

Primary crosslinking was caused to proceed for 10 minutes by heating a mold to 170° C. Hereafter, the molded body was removed from the mold. The removed molded body was subjected to a secondary crosslinking treatment in an oven at 200° C. for 4 hours. In this manner, an evaluation sample of the medical device tube 1 was manufactured.

In the same manner, a molded body conforming to a test piece shape of an evaluation test to be described below was also manufactured.

Examples 2 to 4

An evaluation sample of Example 2 was manufactured in the same manner as in Example 1 except that the content of the liquid fluorine-based elastomer was 15 parts by mass, and the content of the fillers was 1 part by mass. However, as shown in [Table 2], the Mooney viscosity $ML_{1-10}$ (100° C.) of the compound of Example 2 was 39 M.

An evaluation sample of Example 3 was manufactured in the same manner as in Example 1 except that the content of the liquid fluorine-based elastomer was 30 parts by mass, and the filler was changed to flat clay. However, as shown in [Table 2], the Mooney viscosity $ML_{1-10}$ (100° C.) of the compound of Example 3 was 32 M.

ST filler ST-501(product name; commercially available from Shiraishi Calcium Kaisha, Ltd.) was used as the flat clay. An aspect ratio and average particle size of ST-501 were 5 to 50, and 7.0 μm, respectively. A specific surface area of ST-501 was 7.1 m$^2$/g, and was in a range of 3 m$^2$/g or more and 10 m$^2$/g or less.

An evaluation sample of Example 4 was manufactured in the same manner as in Example 1 except that the content of the liquid fluorine-based elastomer was 45 parts by mass, and the filler was changed to flat mica. However, as shown in [Table 2], the Mooney viscosity $ML_{1-10}$ (100° C.) of the compound of Example 4 was 31 M.

Micro mica MK-200 (commercially available from Katakura & Co-op Agri Corporation) was used as flat mica. An aspect ratio and average particle size of MK-200 were 10 to 100, and 5.8 μm to 8.2 μm, respectively. A specific surface area of MK-200 was 6.2 m$^2$/g, and was in a range of 3 m$^2$/g or more and 10 m$^2$/g or less.

Comparative Examples 1 to 6

An evaluation sample of Comparative Example 1 was manufactured in the same manner as in Example 1 except that the fillers were changed to a needle-like alumina. However, as shown in [Table 2], the Mooney viscosity $ML_{1-10}$ (100° C.) of the compound of Comparative Example 1 was 33 M.

Regarding the needle-like alumina, Serra-sur BMI (product name; commercially available from Kawai Lime Industry Co., Ltd.) was used. An aspect ratio and average particle size of Serra-sur BMI were 40 and 6 μm, respectively. A specific surface area of BMI was 30 m$^2$/g.

An evaluation sample of Comparative Example 2 was manufactured in the same manner as in Example 1 except that the fillers were changed to spherical silica. However, as shown in [Table 2], the Mooney viscosity $ML_{1-10}$ (100° C.) of the compound of Comparative Example 2 was 31 M.

Regarding the spherical silica, Min-U-Sil (registered trademark) #5 (product name; commercially available from U.S. Silica Company) was used. The average particle size of Min-U-Sil #5 was 1.6 μm. Since Min-U-Sil #5 was spherical, the aspect ratio was 1. The specific surface area of Min-U-Sil #5 was 1.7 m$^2$/g.

An evaluation sample of Comparative Example 3 was manufactured in the same manner as in Example 1 except that the content of the fillers was changed to 0.1 parts by mass. However as shown in [Table 2], the Mooney viscosity $ML_{1-10}$ (100° C.) of the compound of Comparative Example 3 was 27 M.

An evaluation sample of Comparative Example 4 was manufactured in the same manner as in Example 1 except that the content of the fillers was changed to 8 parts by mass, however, as shown in [Table 2], the Mooney viscosity $ML_{1-10}$ (100° C.) of the compound of Comparative Example 4 was 45 M.

An evaluation sample of Comparative Example 5 was manufactured in the same manner as in Example 1 except that the content of the liquid fluorine-based elastomer was 5 parts by mass. However, as shown in [Table 2], the Mooney viscosity $ML_{1-10}$ (100° C.) of the compound of Comparative Example 5 was 47 M.

An evaluation sample of Comparative Example 6 was manufactured in the same manner as in Example 1 except that the content of the liquid fluorine-based elastomer was 60 parts by mass. However, as shown in [Table 2], the Mooney viscosity $ML_{1-10}$ (100° C.) of the compound of Comparative Example 6 was 20 M.

[Evaluation Method 1]

As shown in [Table 1], in order to evaluate the elastomer molded bodies for a medical device of Examples 1 to 4 and Comparative Examples 1 to 6, the coefficient of friction was measured, the 100% modulus was measured, the perforation strength was evaluated, and the hardness was measured.

In addition, as shown in the above [Table 2] and the following [Table 3], the distribution and orientation of the fillers in the evaluation sample were evaluated.

TABLE 3

|  | DEGREE OF ORIENTATION OF FILLER I(300)/I(116) | PEAK INTENSITY (a.u.) | |
| --- | --- | --- | --- |
|  |  | (300) PLANE | (116) PLANE |
| EXAMPLE 1 | 0.36 | 0.25 | 0.70 |
| COMPARATIVE EXAMPLE 1 | 0.39 | 0.20 | 0.51 |
| SPHERICAL ALUMINA ALONE | 0.09 | 0.05 | 0.55 |

The coefficient of friction was measured as a coefficient of dynamic friction according to the test of a coefficient of friction based on JIS K7125. Therefore, in addition to the evaluation sample of the tube shape described above, test pieces based on JIS K7125 were manufactured using the elastomer molded bodies for a medical device of the examples and the comparative examples.

The test speed was 100 (mm/min), and the test load was 200 g.

A lower coefficient of dynamic friction indicated better slipperiness. When the coefficient of dynamic friction was less than 0.8, the slipperiness was evaluated as very good. When the coefficient of dynamic friction was 0.8 or more and less than 1.0, the slipperiness was evaluated as good. When the coefficient of dynamic friction was 1.0 or more, the slipperiness was evaluated as not good.

The 100% modulus was measured according to a tensile test based on JIS K6251. Therefore, in addition to the evaluation sample of the tube shape described above, dumbbell-like test pieces based on JIS K6251 were manufactured according to the elastomer molded bodies for a medical device of the examples and the comparative examples.

The test speed was set to 500 mm/min, and the stress of the test piece at 100% elongation was measured.

A lower 100% modulus indicated better flexibility. When the 100% modulus was 2.8 MPa or less, the flexibility was evaluated as very good. When the 100% modulus was larger than 2.8 MPa and 4.0 MPa or less, the flexibility was evaluated as good. When the 100% modulus exceeded 4.0 MPa, the flexibility was evaluated as not good.

In order to evaluate the perforation strength, a test piece with a thickness of 0.5 mm, and a pin with a tip R of 0.75 mm were prepared. The mass of the pin was 50 g. The pin was dropped onto the test piece from a predetermined height. Hereafter, air of 0.5 kgf/cm$^2$ (4.9 N/cm$^2$) was applied from one side of the test piece and it was checked whether air leaked. When no air leakage was confirmed, the same pin was dropped from a higher position, and the same measurement was performed. In this manner, a falling height (mm) for the pin in a range in which no air leakage occurred was measured.

In order to evaluate the perforation strength, a falling height for a pin in a range in which no air leakage occurred was used as an index. A higher falling height indicated better perforation strength. When the falling height was 100 mm or more, the perforation strength was evaluated as very good. When the falling height was 80 mm or more and less than 100 mm, the perforation strength was evaluated as good. When the falling height was less than 80 mm, the perforation strength was evaluated as not good.

The hardness was measured based on JIS K6253. Therefore, in addition to the evaluation sample of the tube shape described above, test pieces based on JIS K6253 were manufactured according to the elastomer molded bodies for a medical device of the examples and the comparative examples.

A lower hardness indicated better flexibility. When the hardness was less than 70 Shore A, the hardness was evaluated as good. When the hardness was 70 Shore A or higher, the hardness was evaluated as not good.

In comprehensive evaluation, when "not good" was included in evaluations of the coefficient of friction, the 100% modulus, the perforation strength, and the hardness, it was evaluated as not good (in [Table 1], described as "C"), and when "not good" was not included in evaluations thereof, it was evaluated as good (in [Table 1], described as "A").

In evaluation of distribution in the evaluation sample, through X-ray photoelectron spectroscopy, an amount of the main component element of the filler was measured on the surface and side the evaluation sample. A ratio of weight % of the main component element on the surface to weight % of the inside main component element was calculated as a "filler surface abundance." Here, the surface is a region from the surface layer of the sample to 20 μm to 30 μm, and the inside is a layer 30 μm deeper from the surface layer.

The main component element of the filler was Al in the case of alumina, silica and clay as a silicate mineral, and Si in the case of mica.

In order to evaluate the orientation, a degree of orientation I(300)/I(116) of filler was measured using an X-ray diffraction method. Here, I(300) represents an intensity peak value in the (300) plane, and I(116) represents an intensity peak value in the (116) plane.

Degrees of orientation of Example 1 and Comparative Example 1 were measured. For reference, a degree of orientation of a spherical alumina alone was also measured. Measurement of a spherical alumina alone was performed as follows. Spherical alumina particles were put into an agate mortar, ethanol was added dropwise thereto, and the mixture was then lightly rubbed with a pestle to adjust the particle size. A degree of orientation of the spherical alumina particles having the adjusted particle size that were placed on a slide glass was measured according to the same X-ray diffraction method as described above.

[Evaluation Results 1]

As shown in [Table 1], the coefficients of friction in Examples 1, 2, 3, and 4 were 0.72, 0.76, 0.82, and 0.85, respectively. Therefore, Examples 1 and 2 were evaluated as very good, and Examples 3 and 4 were evaluated as good.

On the other hand, since the coefficients of friction in Comparative Examples 1 to 6 were distributed in a range of 1.2 to 1.5, all of them were evaluated as not good.

Since the 100% moduli in Examples 1 to 4 were distributed in a range of 3.0 MPa to 4.0 MPa, all of them were evaluated as good.

On the other hand, Comparative Examples 1 and 3 were evaluated as good, Comparative Example 6 was evaluated as very good, and Comparative Examples 2, 4, and 5 were evaluated as not good.

The perforation strengths in Examples 1, 2, 3, and 4 were 100 mm, 110 mm, 80 mm, and 80 mm, respectively. Therefore, Examples 1 and 2 were evaluated as very good, and Examples 3 and 4 were evaluated as good.

On the other hand, Comparative Examples 1, 2, and 6 were evaluated as not good, Comparative Example 3 was evaluated as good, and Comparative Examples 4 and 5 were evaluated as very good.

Since the hardnesses of Examples 1 to 4, Comparative Examples 1 to 3, 5, and 6 were all less than 70 Shore A, all of them were evaluated as good. Since Comparative Example 4 had a hardness of 70 Shore A, it was evaluated as not good.

In comprehensive evaluation, Examples 1 to 4 were evaluated as good (A), and Comparative Examples 1 to 6 were evaluated as not good (C).

As shown in [Table 2], the filler surface abundances in Example 1, and Comparative Examples 1 and 2 were 3.3%, 1.4%, and 1.0%, respectively. Therefore, it was understood that, even if the content of the filler was the same, a more remarkable amount of filler was present on the surface in Example 1 than in Comparative Examples 1 and 2.

In this manner, it was thought that, when a larger amount of the filler was distributed on the surface, the coefficient of friction of Example 1 was lower and the perforation strength was unproved.

As shown in [Table 3], it was understood that, comparing the degree of orientation of Example 1 and the degree of orientation of Comparative Example 1, even if the shape of the filler differed, if the aspect ratio was in an appropriate range, the filler was oriented.

Next, Examples 5 to 14 in which the type of crosslinked fluorine-based elastomer, and additive components were variously modified will be described.

The compositions of the elastomer molded bodies for a medical device of examples are shown in the following [Table 4].

specific gravity (20° C.), and viscosity (30° C.) of TAIC were 249, 1.16, and 80 mPa·s to 110 mPa·s, respectively.

Examples 6 to 8

An evaluation sample of Example 6 was manufactured in the same manner as in Example 5 except that the same binary copolymer as in Example 1 was used as a crosslinked fluorine-based elastomer, and the content of the crosslinking aid was changed to 4 parts by mass.

An evaluation of Example 7 was manufactured in the same manner as in Example 5 except that the type and content of the crosslinking aid were changed. In Example 7, regarding the crosslinking aid, 4 parts by mass of triallyl cyanurate (TAC) (commercially available from Kayaku Akzo Co., Ltd.) was used. A molecular weight, specific gravity (30° C.), and viscosity (30° C.) of TAC were 249, 1.12, and 12.6 mPa·s, respectively.

An evaluation sample of Example 8 was manufactured in the same manner as in Example 5 except that no crosslinking aid was contained.

Examples 9 to 14

An evaluation sample of Example 9 was manufactured in the same manner as in Example 5 except that the content of the crosslinking aid was changed to 5 parts by mass and 10

TABLE 4

| | MAIN COMPOSITION OF MOLDED BODY | | | | | | |
|---|---|---|---|---|---|---|---|
| | CROSSLINKED FLUORINE-BASED ELASTOMER | | CROSSLINKING AID | | REINFORCING AGENT | | FILLER |
| | PARTS BY MASS | MATERIAL | PARTS BY MASS | MATERIAL | PARTS BY MASS | MATERIAL | PARTS BY MASS |
| EXAMPLE 5 | 100 | TERNARY COPOLYMER | 2 | taic | 0 | — | 0.5 |
| EXAMPLE 6 | 100 | BINARY COPOLYMER | 4 | taic | 0 | — | 0.5 |
| EXAMPLE 7 | 100 | TERNARY COPOLYMER | 4 | TAC | 0 | — | 0.5 |
| EXAMPLE 8 | 100 | TERNARY COPOLYMER | 0 | — | 0 | — | 0.5 |
| EXAMPLE 9 | 100 | TERNARY COPOLYMER | 5 | taic | 10 | SILICA | 0.5 |
| EXAMPLE 10 | 100 | TERNARY COPOLYMER | 4 | taic | 10 | THERMAL BLACK | 0.5 |
| EXAMPLE 11 | 100 | TERNARY COPOLYMER | 6 | taic | 8 | THERMAL BLACK | 0.5 |
| EXAMPLE 12 | 100 | TERNARY COPOLYMER | 8 | taic | 15 | SILICA | 0.5 |
| EXAMPLE 13 | 100 | TERNARY COPOLYMER | 2 | taic | 8 | SILICA | 0.5 |
| EXAMPLE 14 | 100 | TERNARY COPOLYMER | 20 | taic | 3 | THERMAL BLACK | 0.5 |

In the main composition as shown in [Table 4], an evaluation sample of Example 5 was manufactured in the same manner as in Example 1 except that a ternary copolymer was used as a crosslinked fluorine-based elastomer and 2 parts by mass of a crosslinking aid was added. Therefore, the same amount of fillers 3 as in the Example 1 was contained in Example 5. For simplification, in [Table 4], the liquid fluorine-based elastomer, the crosslinking agent, and the colorant are not described.

Regarding the ternary copolymer, a vinylidene fluoride (VdF)-hexafluoropropylene (HFP)-tetrafluoroethylene (TFE) copolymer was used. Specifically, Daiel G-902 (product name; commercially available from Daikin Industries, Ltd.) was used. A fluorine concentration and Mooney viscosity $ML_{1-10}$ (100° C.) of G-902 were 70.5% and 66 M, respectively.

Regarding the crosslinking aid, triallyl isocyanurate (taic) was used. Specifically, regarding taic, TAIC (registered trademark) (product name; commercially available from Nihon Kasei Co., Ltd.) was used. A molecular weight, parts by mass of a reinforcing agent was added. In Example 9, regarding the reinforcing agent, spherical silica was used. Specifically, regarding the reinforcing agent, the above Min-U-Sil #5 was used.

An evaluation sample of Example 10 was manufactured in the same manner as in Example 5 except that the content of the crosslinking aid was changed to 4 parts by mass, and 10 parts by mass of the reinforcing agent was added. In Example 10, regarding the reinforcing agent, thermal black was used. Specifically, regarding the reinforcing agent, Thermax (registered trademark) N990 (product name; commercially available from Cancarb) was used. The particle size of N990 was 250 nm to 350 nm.

An evaluation sample of Example 11 was manufactured in the same manner as in Example 10 except that the content of the crosslinking aid was changed to 6 parts by mass, and the content of the reinforcing agent was changed to 8 parts by mass.

An evaluation sample of Example 12 was manufactured in the same manner as in Example 9 except that the content of the crosslinking aid was changed to 8 parts by mass, and the content of the reinforcing agent was changed to 15 parts by mass.

An evaluation sample of Example 13 was manufactured in the same manner as in Example 9 except that the content of the crosslinking aid was changed to 2 parts by mass, and the content of the reinforcing agent was changed to 8 parts by mass.

An evaluation sample of Example 14 was manufactured in the same manner as in Example 10 except that the content of the crosslinking aid was changed to 20 parts by mass, and the content of the reinforcing agent was changed to 3 parts by mass.

[Evaluation Method 2]

As shown in [Table 5], in order to evaluate the elastomer molded bodies for a medical device of Examples 1, and 5 to 14, in addition to measurement of the coefficient of friction, measurement of the 100% modulus, evaluation of the perforation strength, and measurement of the hardness described above, the tensile strength was measured, the tear strength was measured, and the appearance was evaluated.

In evaluation of the appearance, it was visually determined whether there were foreign substances, break, burning, bending, denting, chipping, color unevenness of the molded body, which were defects causing failures. When there were none of the above defects, the appearance was evaluated as "good" (in [Table 5] described as "A"). When there were any of the defects, the appearance was evaluated as "not good" (in [Table 5], described as "C").

In comprehensive evaluation, when "not good" was included in evaluations of the coefficient of friction, the tensile strength, the tear strength, the 100% modulus, the perforation strength, and the hardness, it was evaluated as no good (in [Table 5], to be described as "C"). In comprehensive evaluation, when the appearance was evaluated as "not good" and other evaluations included "good" or better results, it was evaluated as "fair" (in [Table 5], described as "B"). The reason for this was that the elastomer molded body for a medical device of which the appearance was evaluated as not good could be used for applications in which the appearance was not considered important. In comprehensive evaluation, when "not good" was not

TABLE 5

EVALUATION RESULTS 2

| | COEFFICIENT OF FRICTION | TENSILE STRENGTH (MPa) | TEAR STRENGTH (kN/m) | 100% MODULUS (MPa) | PERFORATION STRENGTH (mm) | HARDNESS (SHORE A) | APPEARANCE | COMPREHENSIVE EVALUATION |
|---|---|---|---|---|---|---|---|---|
| EXAMPLE 1 | 0.72 | 20 | 24 | 3.0 | 100 | 59 | A | A |
| EXAMPLE 5 | 0.91 | 18 | 25 | 1.5 | 100 | 53 | A | A |
| EXAMPLE 6 | 0.73 | 28 | 29 | 3.3 | 90 | 60 | A | A |
| EXAMPLE 7 | 0.80 | 17 | 21 | 2.0 | 80 | 55 | A | A |
| EXAMPLE 8 | 0.92 | 14 | 20 | 1.3 | 80 | 53 | A | A |
| EXAMPLE 9 | 0.88 | 20 | 29 | 2.5 | 100 | 59 | A | A |
| EXAMPLE 10 | 0.79 | 32 | 30 | 2.3 | 150 | 54 | A | A |
| EXAMPLE 11 | 0.90 | 31 | 26 | 2.7 | 100 | 60 | A | A |
| EXAMPLE 12 | 0.89 | 23 | 30 | 2.6 | 90 | 58 | A | A |
| EXAMPLE 13 | 0.82 | 18 | 26 | 2.3 | 130 | 57 | A | A |
| EXAMPLE 14 | 0.92 | 25 | 30 | 2.4 | 110 | 59 | C | B |

The tensile strength was measured according to a tensile test based on JIS K6251. Therefore, in addition to the evaluation sample of the tube shape described above, test pieces based on JIS K6251 were manufactured according to the elastomer molded bodies for a medical device of the examples.

A higher tensile strength indicated better mechanical resistance. When the tensile strength was 20 MPa or more, the tensile strength was evaluated as very good. When the tensile strength as 13 MPa or more and less than 20 MPa, the tensile strength was evaluated as good. When the tensile strength was less than 13 MPa, the tensile strength was evaluated as not good.

The tear strength was measured according to a tear test based on JIS K6252 Therefore, in addition to the evaluation sample of the tube shape described above, angle-shaped test pieces based on JIS K6252 were manufactured according to the elastomer molded bodies for a medical device of the examples.

The test speed was 500 (mm/min), and the maximum strength was measured.

A higher tear strength indicated better mechanical resistance. When the tear strength was 25 kN/m or more, the tear strength was evaluated as very good. When the tear strength was 20 kN/m or a more and less than 25 kN/m, the tear strength was evaluated as good. When the tear strength was less than 20 kN/m, the tear strength was evaluated as not good.

included in the above evaluations and the appearance evaluation, it was evaluated as good (in [Table 5], described as "A").

[Evaluation Results 2]

As shown in [Table 5], since Examples 1, and 5 to 13 were evaluated as "good" or "very good" in all of evaluations according to an evaluation method 2, comprehensive evaluations thereof were all "good."

The comprehensive evaluation of Example 14 was "fair" because the appearance was evaluated as "not good." This is because the content of the crosslinking aid exceeded 10 parts by mass, and thus color unevenness was caused due to the crosslinking aid. However, Example 14 was very suitable for applications of which the appearance was not required but mechanical resistance was required, for example, an O-ring, because the tensile strength, the tear strength, the 100% modulus and the perforation strength were evaluated as "very good" and the hardness was evaluated as "good."

Example 10 had the largest number of evaluations of "very good."

In particular, Example 5 and Examples 7 to 14 in which a ternary copolymer was used as a main agent had a lower 100% modulus than Example 1 and Example 6 in which a binary copolymer was used as a main agent. Therefore, it was understood that, when a main agent contained a ternary copolymer, the flexibility was superior.

It was understood that, when taic was used as a crosslinking aid, the tear strength was better than that of Example 7 in which TAC was used and Example 8 in which no crosslinking aid was used.

In particular, Examples 10 and 11 in which the content of thermal black was in a range of less than 50 parts by mass had better tensile strength than that of the molded bodies of the other examples.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An elastomer molded body for a medical device, comprising:
    an elastomer portion containing a crosslinked fluorine-based elastomer; and
    a filler formed from a plurality of particles, each of the plurality of particles having an aspect ratio of 5 or more and specific surface area of 3 $m^2/g$ or more and 10 $m^2/g$ or less, the aspect ratio being defined as a ratio of a dimension in a long axis direction thereof to a dimension in a short axis direction thereof, the filler having an uneven distribution in a surface layer part of the elastomer portion and oriented a direction along a surface of the elastomer molded body.

2. The elastomer molded body for a medical device according to claim 1,
    wherein the plurality of particles contain alumina.

3. The elastomer molded body for a medical device according to claim 2,
    wherein 0.2 parts by mass or more and 1 part by mass or less of the filler is contained with respect to 100 paints by mass of the crosslinked fluorine-based elastomer.

4. The elastomer molded body for a medical device according to claim 1,
    wherein the crosslinked fluorine-based elastomer contains a tertiary copolymer including vinylidene fluoride as a monomer.

5. The elastomer molded body for a medical device according to claim 1,
    wherein the elastomer portion further includes a liquid fluorine-based elastomer that is not crosslinked with the crosslinked fluorine-based elastomer.

6. The elastomer molded body for a medical device according to claim 5,
    wherein 10 parts by mass or more and 50 parts by mass of the liquid fluorine-based elastomer is contained with respect to 100 parts by mass of the crosslinked fluorine-based elastomer.

7. The elastomer molded body for a medical device according to claim 1, further comprising
    greater than 0 parts by mass and 10 parts by mass or less of a crosslinking aid with respect to 100 parts by mass of the crosslinked fluorine-based elastomer.

8. The elastomer molded body for a medical device according to claim 7,
    wherein the crosslinking aid contains triallyl isocyanurate.

9. The elastomer molded body for a medical device according to claim 1, further comprising
    greater than 0 parts by mass and 50 parts by mass or less of a reinforcing agent with respect to 100 parts by mass of the crosslinked fluorine-based elastomer.

10. The elastomer molded body for a medical device according to claim 9,
    wherein the reinforcing agent contains thermal black.

11. A medical device comprising the elastomer molded body for a medical device according to claim 1.

12. A method of manufacturing of the elastomer molded body for a medical device according to claim 1, the method comprising:
    kneading a molding material containing an uncrosslinked fluorine-based elastomer and the plurality of particles having the aspect ratio of 5 or more and the specific surface area of 3 $m^2/g$ or more and 10 $m^2/g$ or less to form a kneaded material having a Mooney viscosity $ML_{1-10}$ (100° C.) of 30 M or more and 40 M or less; and
    injecting the kneaded material into a molding space of a mold at a flow rate of 30 mm/min or more and 150 mm/min or less to mold the kneaded material.

* * * * *